(12) United States Patent
Tashiro et al.

(10) Patent No.: US 7,310,404 B2
(45) Date of Patent: Dec. 18, 2007

(54) RADIATION CT RADIOGRAPHING DEVICE, RADIATION CT RADIOGRAPHING SYSTEM, AND RADIATION CT RADIOGRAPHING METHOD USING THE SAME

(75) Inventors: Kazuaki Tashiro, Ebina (JP); Noriyuki Kaifu, Hachioji (JP); Mikio Nakano, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 90 days.

(21) Appl. No.: 11/084,130

(22) Filed: Mar. 21, 2005

(65) Prior Publication Data
US 2005/0265515 A1    Dec. 1, 2005

(30) Foreign Application Priority Data

Mar. 24, 2004    (JP)    ............... 2004-086884
Mar. 26, 2004    (JP)    ............... 2004-092223

(51) Int. Cl.
*G01N 23/00*    (2006.01)
*H05G 1/60*    (2006.01)

(52) U.S. Cl. ................ 378/10; 378/15; 378/19; 378/20

(58) Field of Classification Search ............ 378/10, 378/15, 19, 20
See application file for complete search history.

(56) References Cited

U.S. PATENT DOCUMENTS

| | | | |
|---|---|---|---|
| 4,032,789 A | 6/1977 | Workman | 250/445 |
| 4,211,926 A * | 7/1980 | Nakaya et al. | 378/20 |
| 4,348,589 A * | 9/1982 | Vis | 250/387 |
| 4,600,998 A * | 7/1986 | Huet | 702/40 |
| 4,643,580 A | 2/1987 | Gross et al. | 356/440 |
| 5,012,498 A * | 4/1991 | Cuzin et al. | 378/22 |
| 5,023,895 A * | 6/1991 | McCroskey et al. | 378/4 |
| 5,119,408 A * | 6/1992 | Little et al. | 378/4 |
| 5,530,238 A | 6/1996 | Meulenbrugge et al. | 250/208.1 |

(Continued)

FOREIGN PATENT DOCUMENTS

EP    0 544 505 A2    6/1993

(Continued)

OTHER PUBLICATIONS

Patent Abstracts of Japan, vol. 2000, No. 24 (2001).

*Primary Examiner*—Edward J. Glick
*Assistant Examiner*—Thomas R. Artman
(74) *Attorney, Agent, or Firm*—Fitzpatrick, Cella, Harper & Scinto

(57) ABSTRACT

An object rotating type cone beam radiation CT radiographing device in which a high speed and high sensitivity are obtained with low costs is provided. Thus, a radiation CT device of high performance for vehicle-mounted use and group medical examination can be provided at low costs. In the object rotating type cone beam radiation CT radiographing device, a rotational angle of an object is detected, a signal storage period of a batch-exposure type radiation image sensor panel is controlled on the basis of the rotational angle signal, and a signal storage period of a signal storage type reference signal generator is controlled. There is provided a radiation CT radiographing device in which the object can be photographed at arbitrary resolution during the photographing, a fluctuation of a radiation source during the photographing can be detected without using a special detector and corrected in accordance with its detection amount.

14 Claims, 19 Drawing Sheets

U.S. PATENT DOCUMENTS

| | | | |
|---|---|---|---|
| 5,583,903 A | 12/1996 | Saito et al. | 378/19 |
| 5,764,721 A * | 6/1998 | Light et al. | 378/4 |
| 6,072,851 A | 6/2000 | Sivers | 378/15 |
| 6,148,058 A * | 11/2000 | Dobbs | 378/19 |
| 6,196,715 B1 | 3/2001 | Nambu et al. | 378/197 |
| 6,289,074 B1 | 9/2001 | Arai et al. | 378/4 |
| 6,327,328 B1 | 12/2001 | Satoh et al. | 378/17 |
| 6,381,299 B1 | 4/2002 | Baba et al. | 378/24 |
| 6,470,068 B2 * | 10/2002 | Cheng | 378/20 |
| 6,859,232 B1 | 2/2005 | Hiromichi et al. | 348/302 |
| 6,904,126 B2 * | 6/2005 | Endo | 378/98.8 |
| 6,920,195 B2 * | 7/2005 | Ohishi et al. | 378/10 |

FOREIGN PATENT DOCUMENTS

| | | |
|---|---|---|
| JP | 3-272276 A | 12/1991 |
| JP | 5-042132 A | 2/1993 |
| JP | 5-037267 B2 | 6/1993 |
| JP | 6-276529 A | 9/1994 |
| JP | 8-154926 A | 6/1996 |
| JP | 2000-217810 A | 8/2000 |
| JP | 2001-194461 | 7/2001 |
| JP | 2003-066149 A | 3/2003 |

* cited by examiner

OUTPUT RESPONSE TO Δθ FROM ENCODER

N-th PROJECTION | N+1 th PROJECTION

STORAGE PERIOD

T1 | T2

ΦSH1

ΦRES

ΦCL

ΦSH2

CLOCK

REFERENCE (VIEWING IN A-DIRECTION)

RADIATION CT RADIOGRAPHING DEVICE, RADIATION CT RADIOGRAPHING SYSTEM, AND RADIATION CT RADIOGRAPHING METHOD USING THE SAME

BACKGROUND OF THE INVENTION

1. Field of the Invention

The invention relates to a radiation CT (Computed Tomography) radiographing device for tomography photographing an object, a radiation CT radiographing system, and a radiation CT radiographing method using such a device and a system. More particularly, the invention relates to a cone beam radiation CT radiographing device using a 2-dimensional radiation image sensor panel. Further, the invention relates to a cone beam radiation CT radiographing device of an object rotating type by which an object such as an organism or the like in the state of standing on a floor or sitting on a chair is rotated and photographed between a radiation source and a radiation image sensor facing each other.

2. Related Background Art

In recent years, digitization has been progressed in various medical fields. Also in the X-ray diagnosis field, to digitize an image, there has been developed a 2-dimensional X-ray image pick-up device in which an incident X-ray is converted into visible light by a scintillator (phosphor) and the visible light image is further picked up by an image pick-up element.

The following advantages of the digital X-ray radiographing device over an analog photographing technique exist: elimination of films (filmless system), increase in information obtained by image processes, creation of a database, and the like.

In the field of an X-ray still image, as a 2-dimensional X-ray image pick-up device, for example, a still image pick-up device (flat panel detector) of a large plate of a size of 17 inches (43 cm×43 cm) using amorphous silicon (a-Si) has been manufactured as a device for photographing a breast and a chest region.

In the field of an X-ray motion image, the following device and system have also been proposed: a 2-dimensional digital X-ray radioscopic device in which an incident X-ray is converted into visible light by the scintillator (phosphor) and an I.I. (image intensifier) and the visible light image is picked up by a TV camera using a CCD type image pick-up element; and a system in which the TV camera is replaced by the flat panel detector.

Further, the flat panel detector can also be applied to the X-ray CT radiographing device. Japanese Patent Application Laid-open No. 2001-194461 discloses a technique in which the flat panel detector is applied to a general X-ray CT radiographing device in which an object lying on its side on a bed is photographed while an X-ray valve and a detector, which are arranged so as to face each other, are rotated around the object.

There has also been proposed a device in which a rotating plate that can rotate a human body in the standing or sitting state is provided in order to perform a lung cancer medical examination for a generally healthy person, and the human body is photographed while the rotating plate is rotated for an X-ray source and a 2-dimensional X-ray image pick-up device such as I. I. TV camera, flat panel detector, or the like. Such a device has been disclosed in Japanese Patent Application Laid-open No. H5-42132, Japanese Patent Application Laid-open No. 2000-217810, and the like. In FIG. 12, reference numeral 1 denotes an X-ray CT device as an example of such a device; 2 a scanner unit; 5 a rotating plate on which an object R is mounted; 6 an X-ray source; 7 an image intensifier (I. I.); 3 a processing circuit having a preliminary processing unit 8 and an image reconstructing unit 9; and 4 a display.

In the device, the photographing of the object can be promptly started in the state where the object is standing and can be replaced by the next object in a short time, so that the whole photographing time can be shortened. Further, since the photographing can be completed by at most one rotation by using a cone beam X-ray, radiation exposure dosage of the object can be reduced and the like. Therefore, such a device is preferable as a system suitable for a medical examination. Since a gantry to integratedly rotate the X-ray source and the X-ray detector is unnecessary, the positions of the X-ray source and the X-ray detector can be freely set, and an enlargement ratio upon measurement and a measuring region can be changed. Since the X-ray source for general photographing can be used and the gantry is unnecessary, the costs of the system can be suppressed. Further, since a construction of the system is simple, it is advantageous for vehicle-mounted use.

As a feature of a cone beam X-ray CT radiographing device which will be mentioned in the invention, a detector merely rotates on a rotary axis and is not moved in the rotary axial direction. Therefore, if there is a 2-dimensional detector of a large plate which can grasp the whole pertinent region of the object, all projection image data to reconstruct the whole CT image can be obtained by one rotation.

In the case where the conventional object rotating type cone beam X-ray CT radiographing device is used for a medical field, it is demanded to shorten restriction time of a human body serving as an object as much as possible. As a method of shortening a holding time of the same posture of the object, that is, a time that is required for measurement, there is a method of raising a rotating speed of the object. However, a time of about 5 seconds or longer is necessary for rotating the object once. There is a problem that if the object is rotated at a speed higher than such a rotating time, the object enters what is called a dizzy state where he feels dizzy.

There is also a problem that when the object is rotated at a high speed, a centrifugal force which is applied to the object also increases together with an increase in rotating speed, so that the object is moved during the measurement.

It may be necessary for the object being photographed to hold his breath during photographing depending on a photographing region. In the case of photographing a region where a body's movement due to a breath is large, particularly, upon photographing a chest region or the like, the breath must be held. There is also a problem that since the breath pausing time of about 5 seconds per rotation is relatively long, an examinee feels anxiety during the examination, a body movement artifact occurs due to an unexpected operation, body vibration, or the like, or the object is out of a field of vision of the detector, so that the photographing fails.

There is also a problem that if the object is moved during the measurement, "blur" or "deflection" occurs in a 3-dimensional X-ray distribution image formed by the reconstruction and picture quality of a 3-dimensional X-ray image deteriorates.

In the case of rotating the rotating plate on which the object with a considerable weight is mounted, it takes time until the rotating speed reaches a predetermined speed and becomes stable. There is, consequently, a problem that more than one rotation is necessary and a burden on the patient becomes heavy.

There is also a problem that if the photographing is started in the unstable state, rotational angles of respective projections differ, precision of the reconstruction deteriorates, a variation in a signal from a reference element increases, precision of the correction deteriorates, and the image deteriorates.

There is also a problem that, generally, in the X-ray CT radiographing device, even if the X-ray is radiated while a lamp voltage and a lamp current are set to the same conditions, upon photographing, X-ray intensity actually changes for every scanning, in detail, and in every viewing. This problem is caused by focal position changes or the like due to expansion/contraction of a shaft of an anode by a temperature change of an X-ray valve, movement of the shaft between bearings due to the motion of the valve, precession motion when the anode is rotating, and the like. As countermeasures against those problems, in the conventional single slice type X-ray CT radiographing device and the conventional multi slice type X-ray CT radiographing device, a method whereby a reference channel to measure the intensity of the X-ray which does not transmit the object in the X-ray from the X-ray valve is arranged in the edge portion of the X-ray detector, each channel value is corrected by using a value measured by the reference channel, and data to form an image is often used. However, there is also a similar problem in the object rotating type cone beam X-ray CT radiographing device.

There is also a problem that a complicated mechanism and control apparatus are necessary to rotate the rotating plate on which various objects are mounted while it is precisely controlled, so that the manufacturing costs rise.

There is also such a problem that in the case where the rotating plate on which the object is mounted is photographed while purposely changing the rotating speed in dependence on the photographing region of the object, an accurate image of each region cannot be obtained corresponding to each rotating speed set for every photographing region of the object.

Further, if the object is rotated by 360° for 5 seconds and photographed by the full scan by 1000 projections, images have to be read out for 5 msec per projection, that is, at a speed of 200 frames/sec. However, there is such a problem that it is very difficult to drive the flat panel detector using a thin film transistor of a-Si or a-Se with an area of the 17-inch size (43 cm×43 cm) or more at such a speed because semiconductor characteristics of a-Si or a-Se are inadequate.

There is such a problem that in the cone beam X-ray CT radiographing device in which an X-ray dosage per projection is fairly smaller than that of the still image, since noises are large and the sensitivity is low, the sensitivity in the conventional flat panel detector is insufficient.

The I. I. TV camera, which is advantageous in terms of the sensitivity, has problems peculiar to the image intensifier. That is, there are the following problems: an essential problem in which a distortion of the image occurs in the peripheral portion; a problem in which even in the current maximum 17-inch size, since the display screen is circular, an wide enough area almost equal to that of the flat panel detector cannot be obtained, the reconstructing area decreases remarkably in the cone beam X-ray CT; and a problem in which, since the magnetism is used for controlling an electron beam, if the device is rotated, it is complicatedly influenced by the terrestrial magnetism.

In Japanese Patent Application Laid-open No. H5-42132, nothing is considered with respect to countermeasures against the fluctuation of the X-ray source, rotational drift, and body movement in the case of rotating the object. In Japanese Patent Application Laid-open No. 2000-217810, only a measure against the body movement is taken and nothing is considered with respect to countermeasures against the fluctuation of the X-ray source and the rotational drift. Further, in Japanese Patent Application Laid-open No. 2001-194461, countermeasures against the reading speed and the sensitivity which are required in the object rotating type cone beam X-ray CT radiographing device are not disclosed.

Moreover, in Japanese Patent Application Laid-open No. 2003-66149, a multi slice X-ray CT radiographing device in which detectors having a plurality of resolution are arranged is disclosed.

The X-ray source for general photographing can be used in the object rotating type cone beam X-ray CT radiographing device. However, the following problems of the X-ray source exist.

That is, in an X-ray valve, an electron beam is radiated to a target so as to generate an X-ray. If a material of the target is tungsten, converting efficiency of an energy of the electron beam into the X-ray is less than 1% and most of the remaining portion of the energy changes into a thermal energy. Therefore, since a temperature of the target becomes high, a rotating anode is generally used as a countermeasure against such a problem.

The rotating anode has a conical shape and the electron collides with the side surface of the rotating anode. Although most of the heat generated in the target is radiated as a radiation energy to the circumference from the target, a part of the generated heat is radiated by thermal conduction through a rotary shaft. By repeating the X-ray radiation, a quantity of heat which is accumulated in the target in the X-ray tube increases and a temperature of the rotary shaft or the like rises. It has been known that thermal expansion is caused in the target by such a temperature increase.

A focal position is deviated by a positional deviation of the rotary electrode and the cathode and a positional deviation in the flying direction of the electron beam. Since such a phenomenon is caused due to a temperature change, aging change, abrasion of the electrode, or the like, it is impossible to avoid the situation wherein the focal position differs by a difference of the time position upon collection of X-ray absorption data, that is, by a difference of the X-ray exposing time point. In the case of the X-ray CT radiographing, a geometrical positional relation among the focal position of the X-ray source, the rotary shaft, and the detector is very important.

A fluctuation of sensitivity distribution of the detector due to the movement of the focal point becomes a calibration error resulting in an artifact on the reconstructed image. It is, therefore, necessary to correct the change in detection output of the X-ray detector due to such a deviation of the focal position. Therefore, a reference detector is prepared to monitor the X-ray intensity. For example, a reference element and correction in the general multi slice X-ray CT radiographing device have been disclosed in Japanese Patent Application Laid-open No. H8-154926. FIGS. 20A and 20B show such a conventional technique. In FIGS. 20A and 20B, reference numeral 25 denotes a reference detector as mentioned above; 23 an image detector; 24 a focal point; 27 an object; and 20 a collimator.

In the case where the object rotating type cone beam X-ray CT radiographing device is used for the medical examination, it is necessary to shorten the restriction time of the human body serving as an object as much as possible. A method of raising the rotating speed of the object can be mentioned as a method of shortening the holding period of the same posture of the object, that is, the time which is required for measurement. However, in the case of rotating the object at a high speed, the object enters what is called a dizzy state where he feels dizzy. It is, therefore, known that about 3 to 5 seconds are necessary as a time which is required for one rotation of the object.

Naturally, the X-ray has to be radiated from the X-ray source for such a period of time and the focus movement mentioned above becomes a problem. Moreover, since a countermeasure against the continuous photographing of a long period of time is not taken in the X-ray source for the general photographing, such a problem is more serious than that in the case of the X-ray source only for the X-ray CT radiographing. There is also such a problem that when the existing X-ray source is used, there are various histories and the change in age, abrasion of the electrode, and the like, which also differ with every device, so that it has to cope with them for every X-ray source. Further, since the X-ray source for the general photographing is not equipped with the foregoing reference detector, the reference detector has to be separately prepared and installed in the case of constructing the system.

On the other hand, according to the technique disclosed in Japanese Patent Application Laid-open No. 2003-66149, only the fixed resolution can be obtained. In Japanese Patent Application Laid-open No. 2000-217810, nothing is disclosed with respect to the problems which are caused by the focus movement of the X-ray source in the object rotating type cone beam X-ray CT radiographing device. In the detecting method of the focus movement in Japanese Patent Application Laid-open No. H8-154926, nothing is disclosed with respect to the precision of the beam detection and since substantially the same detector as the main detector is used, the beam can be detected only at the same column width as that of the main detector.

SUMMARY OF THE INVENTION

The invention is made in consideration of the foregoing conventional problems and it is an object of the invention to provide an object rotating type cone beam radiation CT radiographing device and a radiation CT radiographing system in which a high processing speed and high sensitivity are obtained with low costs and to provide a radiation CT radiographing method using such a device and a system. Thus, a radiation CT device of high performance for a vehicle-mounted use or a group medical examination can be provided at low costs.

Further, the invention is made in consideration of the foregoing conventional problems and it is an object of the invention to provide an object rotating type cone beam radiation CT radiographing device and a radiation CT radiographing system in which an object can be photographed at arbitrary resolution and to provide a radiation CT radiographing method using such a device and a system. Moreover, it is an object of the invention to provide an object rotating type cone beam radiation CT radiographing device and a radiation CT radiographing system in which a fluctuation of a radiation source during the photographing is detected without using any special detector and can be corrected in accordance with a detection amount, and to provide a radiation CT radiographing method using such a device and a system.

To solve the above problems, according to the invention, there is provided a radiation CT radiographing device comprising: rotating means for rotating an object while radiating an X-ray to the object; rotational angle detecting means for detecting a rotational angle of the rotating means and generating a rotational angle signal; a radiation image sensor panel for forming projection image data of the object in accordance with the rotation; and means for controlling a signal storage period of the radiation image sensor panel by using the rotational angle signal.

According to the invention, there is provided a radiation CT radiographing device comprising: rotating means for rotating an object around a rotary axis while radiating a radiation to the object; rotational angle detecting means for detecting a rotational angle of the rotating means and generating a rotational angle signal; a radiation image sensor panel for forming projection image data of the object in accordance with the rotation in the state where the radiation image sensor panel is relatively fixed to the rotary axis; and means for controlling a signal storage period of the radiation image sensor panel by using the rotational angle signal.

According to the invention, there is provided a cone beam radiation CT radiographing device comprising: rotating means for rotating an object while radiating a cone beam radiation to the object; rotational angle detecting means for detecting a rotational angle of the rotating means and generating a rotational angle signal; and means for controlling a signal storage period of an image sensor panel by using the rotational angle signal.

According to the invention, there is provided a radiation CT radiographing system comprising: a radiation source for radiating a radiation to an object; means for controlling the radiation source; rotating means for rotating the object; rotational angle detecting means for detecting a rotational angle of the rotating means and generating a rotational angle signal; a radiation image sensor panel for forming projection image data of the object in accordance with the rotation; and means for controlling a signal storage period of the radiation image sensor panel by using the rotational angle signal.

According to the invention, there is provided a radiation CT radiographing method comprising the steps of: rotating an object around a rotary axis while radiating a continuous radiation to the object; detecting a rotational angle signal in accordance with the rotation; controlling a reference signal storage period and a signal storage period of the batch-exposed signal by using the rotational angle signal; and obtaining projection image data corresponding to the rotational angle by a radiation image sensor panel which is relatively fixed to a rotary axis.

To accomplish the above object, according to the invention, in the radiation CT radiographing device, the device has the radiation image sensor panel having an image pick-up element, and the image pick-up element has: a plurality of pixels arranged in a 2-dimensional shape; resolution setting means for setting a plurality of resolution; image signal obtaining means for reading out an image signal of the object; and correcting signal obtaining means for reading out a correcting signal.

According to the invention, there is provided a radiation CT radiographing device comprising a radiation image sensor panel for forming a 2-dimensional projection image signal, wherein the radiation image sensor panel has a plurality of image pick-up elements arranged in a 2-dimensional shape and the image pick-up element has a plurality of pixels and resolution setting means for setting a plurality of resolution on one semiconductor substrate.

According to the invention, there is provided a radiation CT radiographing device comprising a radiation image sensor panel for forming a 2-dimensional projection image signal, wherein the radiation image sensor panel has a plurality of image pick-up elements arranged in a 2-dimensional shape and the image pick-up element has: resolution setting means for setting first resolution and second resolution; image signal storing means for storing the 2-dimensional projection image signal by batch-exposure; and non-destructive reading means provided on a signal output side of the image signal storing means.

According to the invention, there is provided a radiation CT radiographing system comprising: a radiation generator for generating a radiation to an object; a control device of the radiation generator; a radiation image sensor panel for forming a 2-dimensional projection image signal; and means for correcting an image signal, wherein the radiation image sensor panel has a plurality of image pick-up elements arranged in a 2-dimensional shape and the image pick-up element has resolution setting means for setting first resolution and second resolution, image signal storing means for storing the 2-dimensional projection image signal by batch-exposure, and non-destructive reading means provided on a signal output side of the image signal storing means.

According to the invention, there is provided a radiation CT radiographing method comprising the steps of: rotating an object; radiating a continuous radiation to the object; obtaining a 2-dimensional projection image signal of the object by batch-exposure by using a radiation image sensor panel; reading out a part of the 2-dimensional projection image signal at first resolution in a non-destructive manner by non-destructive reading means which the radiation image sensor panel has; detecting a focus movement of the radiation by using the image signal which was read out in the non-destructive manner; and correcting the image signal outputted from output means in accordance with an amount of the detected focus movement.

In the invention, since there is no need to wait until the rotation becomes stable and the wasteful rotation time can be shortened, it is comfortable for the patient. The dedicated reference element is unnecessary. Since the panel can be used as it is, the system is simplified and the costs are reduced. Further, there is no need to prepare the reference element on the X-ray source side. The X-ray source for the general photographing can be used in common. Since it is sufficient to arrange the rotating device and the X-ray image sensor in the general photographing room, the expenses of the facilities can be reduced. Since it is sufficient to use the rotating device with the general mechanism, the costs can be easily reduced. Even if there is a slight rotational variation, it is possible to cope with it. The mechanism for accurately controlling the rotation is unnecessary. Since the system construction is simple, the maintenance is easy to perform and it is convenient to mount the system onto the general examination vehicle.

According to the invention, the object rotating type cone beam radiation radiographing device having high processing speed, high sensitivity, and high performance with low costs can be realized by the X-ray image sensor panel of the large panel size using a plurality of CMOS type image pick-up elements and by the novel driving method. Thus, the radiation CT radiographing device of high performance for a vehicle-mounted use and group medical examination can be provided at low costs.

In the case where the object is photographed while the rotating speed of the rotating plate on which the object is mounted is purposely fluctuated in accordance with the photographing region of the object, by measuring a rotation signal every time and controlling the signal storage period of the radiation image sensor panel, the accurate image can be obtained in correspondence to the rotating speed set every photographing region of the object.

BRIEF DESCRIPTION OF THE DRAWINGS

FIGS. 3A and 3B are diagrams for explaining a conventional reference element and a reference element according to the invention, in which FIG. 3A is an equivalent circuit diagram of the conventional reference element and FIG. 3B is an equivalent circuit diagram of the signal storage type reference element according to the invention;

FIG. 16A is a diagram showing a relation between the focus movement and an edge image, and FIG. 16B is a diagram showing the state where the motion of the edge is detected at high resolution;

DETAILED DESCRIPTION OF THE PREFERRED EMBODIMENTS

Figure 1:
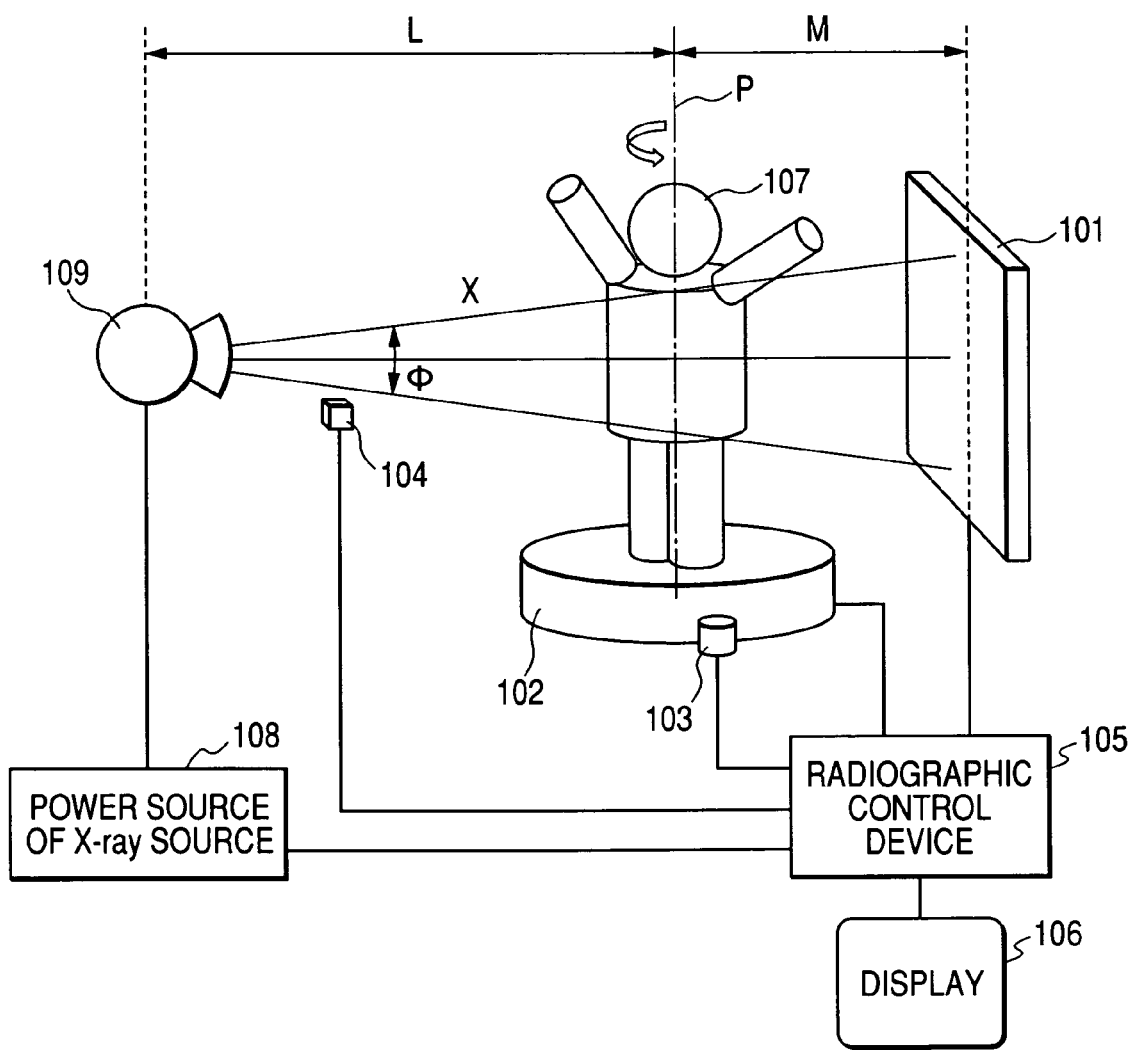
FIG. 1 is a schematic diagram showing the first embodiment of a radiation CT radiographing device according to the invention.

The best mode for carrying out the invention will now be described in detail with reference to the drawings. The component elements having substantially the same functions in all diagrams for explaining the embodiment of the invention are designated by the same reference numerals and their explanation is not repeated for each embodiment.

First Embodiment

FIG. 1 is a diagram for explaining a schematic construction of the first embodiment of an object rotating type cone beam radiation CT radiographing device according to the invention. In the diagram, reference numeral 109 denotes an X-ray generator (X-ray source); 108 a power source for an X-ray source; X a radiated continuous X-ray; 107 an object; 104 a signal storage type reference element; 102 a rotating device (rotating plate); P a rotary axis of the rotating device; 103 a rotary encoder; 101 an X-ray image sensor panel; 105 a radiographic control device; and 106 a display. Although the X-ray is used as a radiation in the embodiment, another radiation such as α-ray, β-ray, γ-ray, or the like can be used. This is true of all embodiments.

The X-ray generator 109 is used for general photographing and is used in a continuous X-ray mode. The radiographic control device 105 sets a lamp voltage, a lamp current, and radiation time and controls only the start and stop of the radiation. A geometrical layout of the X-ray generator 109, rotating plate 102, and X-ray image sensor panel 101 is accurately set. That is, it is set so that a perpendicular drawn from an X-ray focal point to the X-ray image sensor panel passes through the rotary axis. A distance between the X-ray focal point and the rotary axis P of the rotating plate 102 is set to L and a distance between the rotary axis P and the X-ray image sensor panel 101 is set to M. By changing values of L and M, an enlargement ratio of a projection image and a cone angle Φ of a cone beam can be set.

The rotating plate 102 and the X-ray image sensor panel 101 are movable and, after their geometrical layout is determined, they are fixed at the locations of the layout. In the cone beam X-ray CT radiographing device, when the cone angle increases, an error upon reconstruction increases. Therefore, the cone angle Φ is generally set to 10° or less. In this case, the value of L is fairly large and the enlargement ratio of the projection image is smaller than that of the general X-ray CT.

The rotating device 102 is a device for continuously rotating a rotating portion on the basis of a rotation control signal from the radiographic control device 105. A holding device (not shown) to hold the object 107 during the rotation is attached to the rotating portion. The rotary encoder 103 to measure a rotational angle of the rotating device 102 and output it to the radiographic control device 105 is further provided. In the case where the object is photographed by the full scan during one rotation of 360° by 1000 projections, the rotary encoder generates a signal every angle of 0.36° per projection. The rotary encoder measures the angle of the rotation and forms the signal corresponding to the measured angle. The invention is not limited to the rotary encoder 103 but an arbitrary rotational angle detecting means can be used.

In the object rotating type cone beam X-ray CT radiographing device, as mentioned above, if the object is photographed by the full scan during one rotation of 360° for 5 seconds by 1000 projections, it takes a time of 5 msec per projection, so that it is difficult to pulse-drive the X-ray source. Particularly, in the case of using the X-ray source for the general photographing, it is difficult to radiate the stable pulse X-ray because a leading/trailing response speed of the lamp current is low. In the embodiment, therefore, a construction using the continuous X-ray is used. In the radiographing using the cone beam X-ray, since it is necessary to obtain images without a time lag in the whole region for 5 msec and cope with the rotational variation, the X-ray image sensor panel and a signal storage type reference element with a structure, which will be explained hereinafter, are used, thereby preventing such a problem from occurring.

Figure 2:
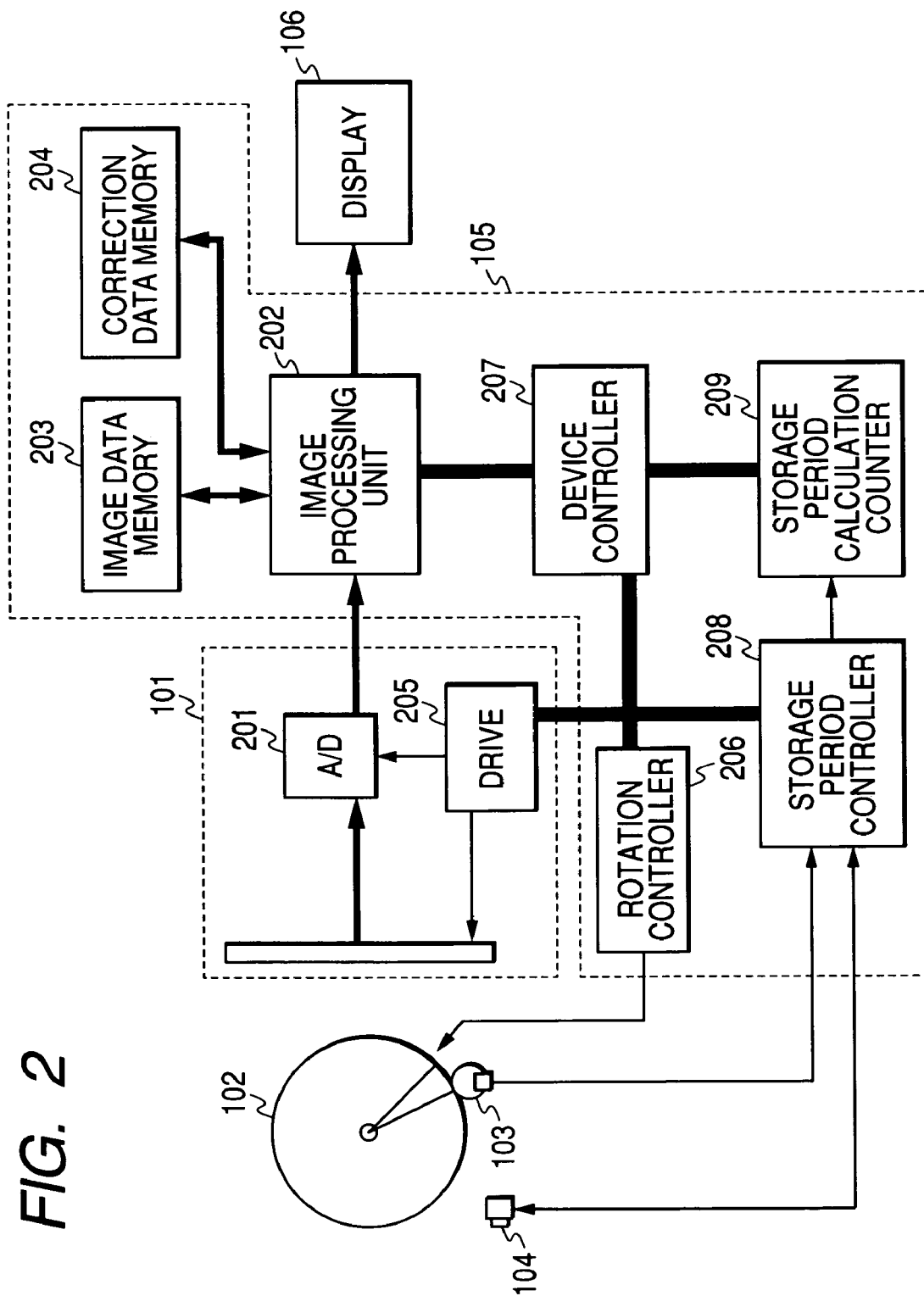
FIG. 2 is a system block diagram showing the first embodiment of the radiation CT radiographing device according to the invention.

FIG. 2 shows a system construction in the embodiment. The radiographic control device 105 includes: an image data memory 203 for storing the projection image data outputted from the X-ray image sensor panel 101; a correction data memory 204 for storing correction data; an image processing unit 202; a device controller 207; a storage period controller 208; a storage period calculation counter 209; and a rotation controller (rotating device controller) 206. The X-ray image sensor panel 101 includes an A/D converter 201 and a drive 205.

The radiographic control device 105 controls the X-ray radiation from the X-ray generator 109 on the basis of photographing conditions input by the observer, controls a visual field mode of the X-ray image sensor panel 101, and controls the number of pixels and a frame rate. The radiographic control device 105 also controls a storage period of each of the signal storage type reference element 104 and the X-ray image sensor panel 101 by the storage period controller 208 on the basis of the signal from the rotary encoder 103.

The image processing unit 202 executes: preliminary processes such as gamma correction, image distortion correction, logarithm conversion, sensitivity variation correction of the X-ray image sensor panel 101, and the like; a reconstruction for forming a 3-dimensional X-ray distribution image as 3-dimensional X-ray absorption coefficient distribution of the object 107 on the basis of a projection image (projection data) after the preliminary processes; and an image process such as well-known volume rendering process, maximum value projecting process, or the like, which is executed to the 3-dimensional X-ray distribution image. The image processing unit 202 forms an X-ray tomogram image or a 3-dimensional X-ray image as a 3-dimensional-like 2-dimensional image from the 3-dimensional X-ray distribution image.

Figure 3A:
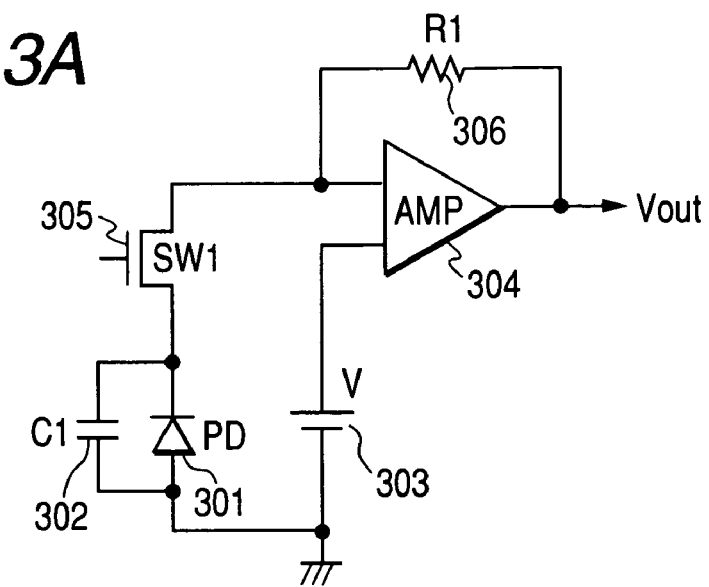

Structures and functions of the signal storage type reference element 104 and the X-ray image sensor panel 101 as features of the embodiment, a relation with the rotary encoder 103, and its functional effects will now be described. FIG. 3A is an equivalent circuit diagram of the conventional general reference element. A photodiode PD (301) converts light emitted by a scintillator (not shown) by the X-ray radiation into an electric signal. A switch SW1 (305) comprising an MOSFET is serially connected to the photodiode PD (301). The switch SW1 (305) is further connected to an inverting terminal of an operational amplifier Amp (304).

A feedback resistor R1 (306) is connected to the operational amplifier Amp (304), thereby constructing a current/voltage converting circuit. An input current is outputted as a voltage signal from the operational amplifier Amp. A voltage V (303) is applied to a non-inverting terminal of the operational amplifier Amp (304) for the ground (GND). When a positive read pulse is inputted to a gate of the switch SW1 (305), the switch SW1 (305) is opened, the photodiode PD (301) enters an anti-bias state, and predetermined charges are charged in a coupling capacitor C1 (302).

Subsequently, when the switch SW1 (305) is closed and the light enters during the storage period, the charged charges are discharged by the charges based on the light incidence. A cathode potential of the photodiode PD (301) approaches the ground potential. An amount of discharged charges increases in proportion to the incident light amount. When the read pulse is subsequently input into the gate of the switch SW1 (305) and the switch SW1 (305) is opened, the charges corresponding to the charges discharged for the storage period are supplied through the feedback resistor R1 (306) and the photodiode PD (301) enters the anti-bias state again and is initialized.

At this time, a potential difference due to the charge current is caused across the feedback resistor R1 (306) and output as a voltage signal from the operational amplifier Amp (304). Since the charge current corresponds to the discharge current based on the light incidence, the incident light amount is detected by this output voltage. The signal according to an X-ray dosage rate at certain time is simply used as mentioned above.

Figure 3B:
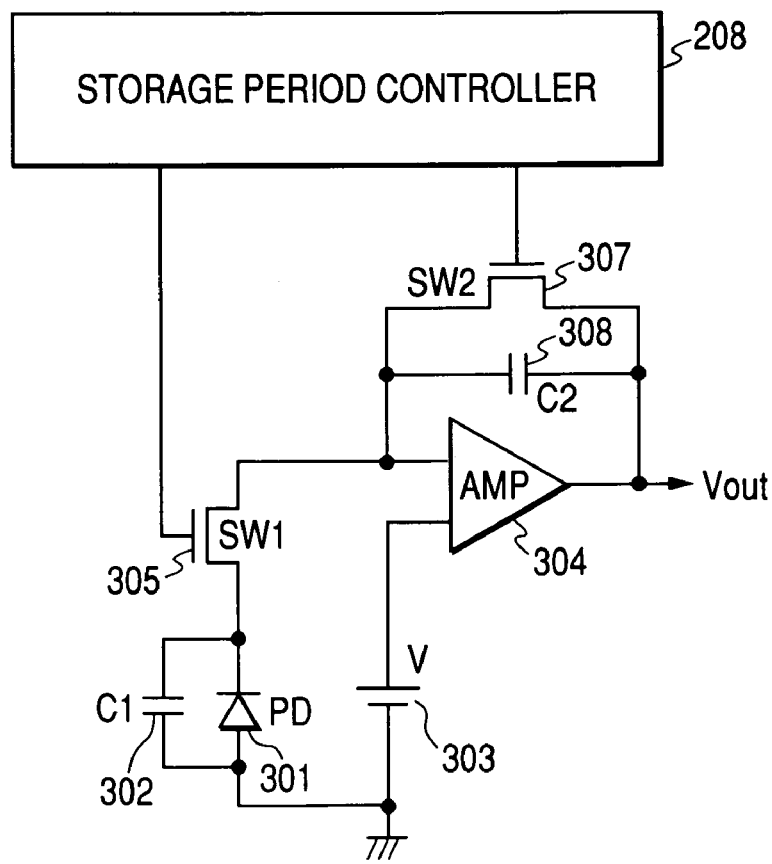

FIG. 3B is an equivalent circuit diagram of the signal storage type reference element according to the embodiment. An integration capacitor C2 (308) and the reset switch SW2 (307) are connected between the inverting terminal of the operational amplifier Amp (304) and the output terminal, thereby constructing a current integrating circuit as a whole. The integration capacitor C2 of the integrating circuit is discharged by an external reset pulse just before the switch SW1 (305) for reading out is opened. Subsequently, when the switch SW1 (305) is opened, the charges corresponding to the light output during the storage period are charged into the coupling capacitor C1 (302) of the photodiode PD. The electric potential of the photodiode PD is initialized to the positive potential V (303). The integration capacitor C2 (308) is also charged by the charge current. Therefore, an integration waveform of a square wave is obtained at an output terminal of the integrating circuit. The switch SW1 (305) for reading out and the reset switch SW2 (307) are driven by the pulse signal formed by the storage period controller 208 on the basis of the angle signal from the rotary encoder 103.

In the case of photographing the object by the full scan during one rotation of 360° by 1000 projections, the rotary encoder 103 generates the rotational angle signal every angle of 0.36° per projection. This signal is sent to the storage period controller 208 and operation timing pulses of the switches SW1 and SW2 are formed on the basis of this signal. Thus, the output signal is stored for the storage period with respect to the angle of one projection. Therefore, even if there is a rotational variation in the rotating plate, the X-ray amount for the time corresponding to the rotational angle per projection which has accurately been determined can be monitored.

The signal storage type reference element 104 is not limited only to the construction shown in the above equivalent circuit. It is possible to use an arbitrary element with a circuit construction which can store the sensor signal within the time set by an external signal and output its integration amount as a signal.

Figure 5:
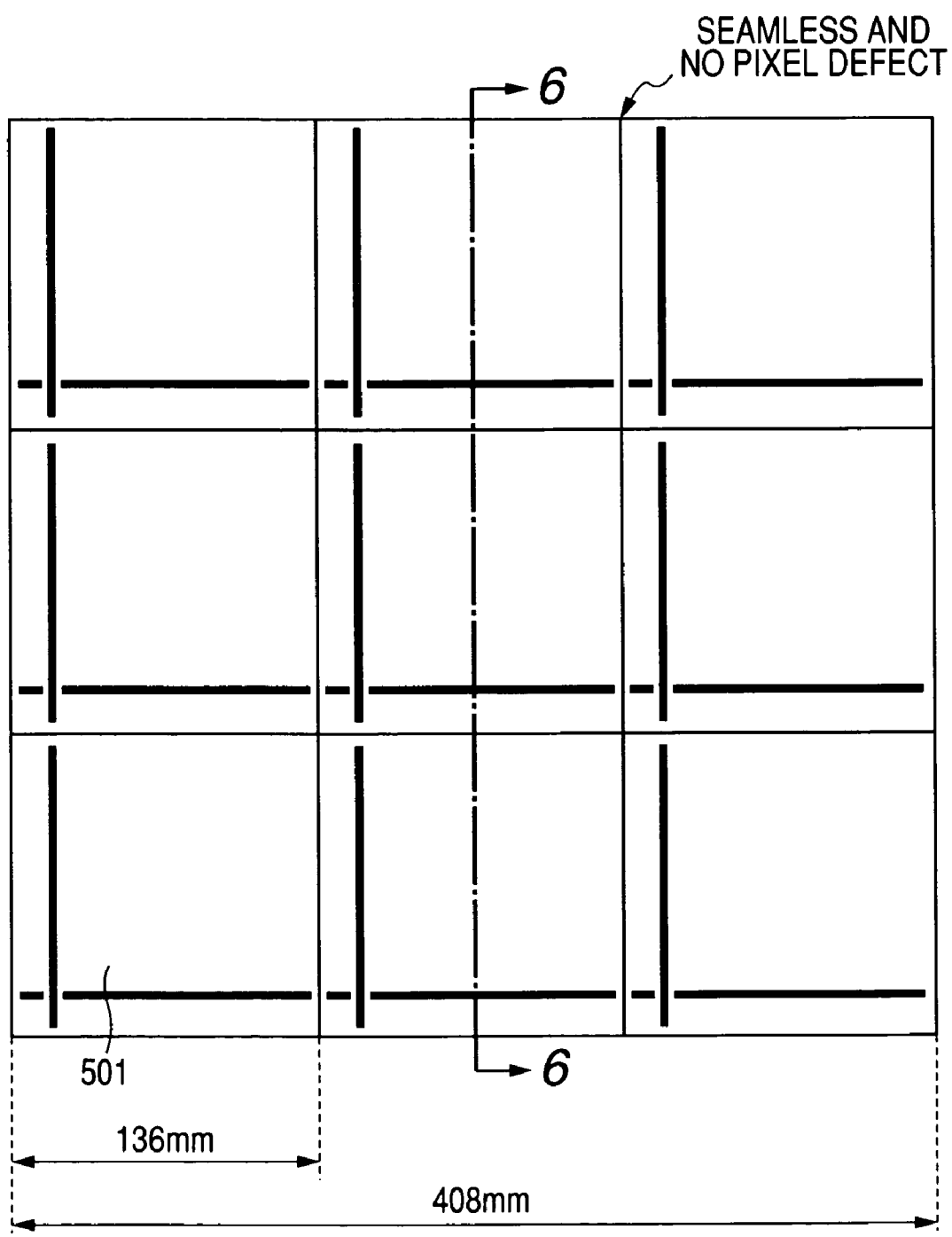
FIG. 5 is a diagram showing an X-ray image sensor panel of the first and fifth embodiments according to the invention.

FIG. 5 shows an X-ray image sensor panel in which a large area of (408 mm×408 mm) is realized by two-dimensionally adhering nine CMOS type image pick-up elements 501 each having a size (136 mm×136 mm) onto one base plate. According to this image sensor panel, since the CMOS type image pick-up elements are used, the charges stored for the common period of time can be read out from all of the elements at a high S/N ratio (signal-to-noise ratio). The image pick-up element mentioned in the specification of the invention denotes an image pick-up element panel on which a plurality of pixels are two-dimensionally arranged. The whole surface of the CMOS image pick-up element panel is a pixel area as will be explained hereinafter. By adhering a plurality of image pick-up element panels onto the base plate, the image pick-up device of a large area which can obtain a seamless image can be realized. There is no limitation in its size in principle.

Figure 6:
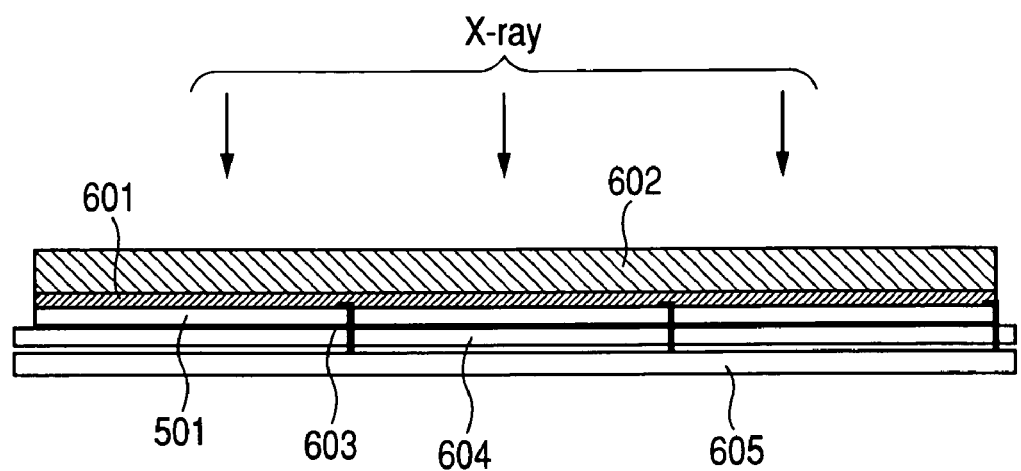
FIG. 6 is a cross sectional view taken along the line 6-6 in FIG. 5.

FIG. 6 shows a cross sectional view taken along the line 6-6 in FIG. 5. A scintillator 602 is made of $Gd_2O_2S$, CsI, or the like using europium, terbium, or the like as a deactivator. In the embodiment, since the X-ray image sensor panel 101 of the large plate is used, a seamless scintillator of the large plate is also used as a scintillator 602. The X-ray image sensor panel is formed by integratedly assembling one scintillator and a plurality of image pick-up elements 501.

Since the X-ray collides with the scintillator 602, it is converted into visible light, and is detected by the image pick-up elements 501, it is preferable to select the scintillator 602 so that its light-emitting wavelength is adapted to the sensitivity of the image pick-up element. Further, it is desirable to increase a thickness of scintillator 602 in order to increase an absorption factor of the x-ray and improve use efficiency. In the case of using $Gd_2O_2S$, it is difficult to form the panel of the large and thick plate. Further, the panel using ordinary powder shows a high X-ray absorption factor and it has the drawbacks that, if it is further thickened, efficiency (DQE: Detective Quantum Efficiency) deteriorates. In the embodiment, therefore, CsI (T1), which is evaporation-deposited onto a resin substrate of a large plate on which a thick film can be easily formed, is used.

In the radiation CT radiographing device for the medical examination, it is sufficient to set a pixel to a large size of about (500 μm×500 μm to 1 mm×1 mm). In the case of the CsI (T1) panel with a thickness of 1 mm, an X-ray absorption factor is equal to 90% or more and the efficiency (DQE) can be maximized within a range of the resolution which is necessary for the X-ray CT. When the thickness is equal to or more than 1.5 mm, the DQE deteriorates steeply. Therefore, the CsI (T1) panel with a thickness of 1 mm is used in the embodiment.

An external processing board 605 has a circuit for supplying a power source, clocks, and the like for the image pick-up elements 501 and extracting and processing the signals from the image pick-up elements 501. A flexible board 603 is used to electrically connect each image pick-up element 501 to the external processing board 605.

The nine image pick-up elements 501 are adhered onto a base plate 604 so that no gaps are substantially formed among the image pick-up elements. The wording "no gaps are substantially formed" denotes that a dropout among the image pick-up elements does not occur in an image which is formed by the nine image pick-up elements. The input of the clocks, power source, and the like of the image pick-up element and the output of the signal from the image pick-up element are executed with the external processing board 605 arranged on the back side of the image pick-up element through the flexible board 603 connected to the electrode pad in the edge portion of the image pick-up element. Since a thickness of flexible board 603 is sufficiently thinner than the size, even if the X-ray is passed through the gap between the image pick-up elements, no defects on the image occur. The output signals from the image pick-up elements are read out in parallel. The high-quality image which is seamless with respect to the time and space and in which there is no time lag every projection can be obtained at a high speed by batch-exposure, which will be explained hereinafter, and the parallel reading operations of the image pick-up elements.

Figure 7:
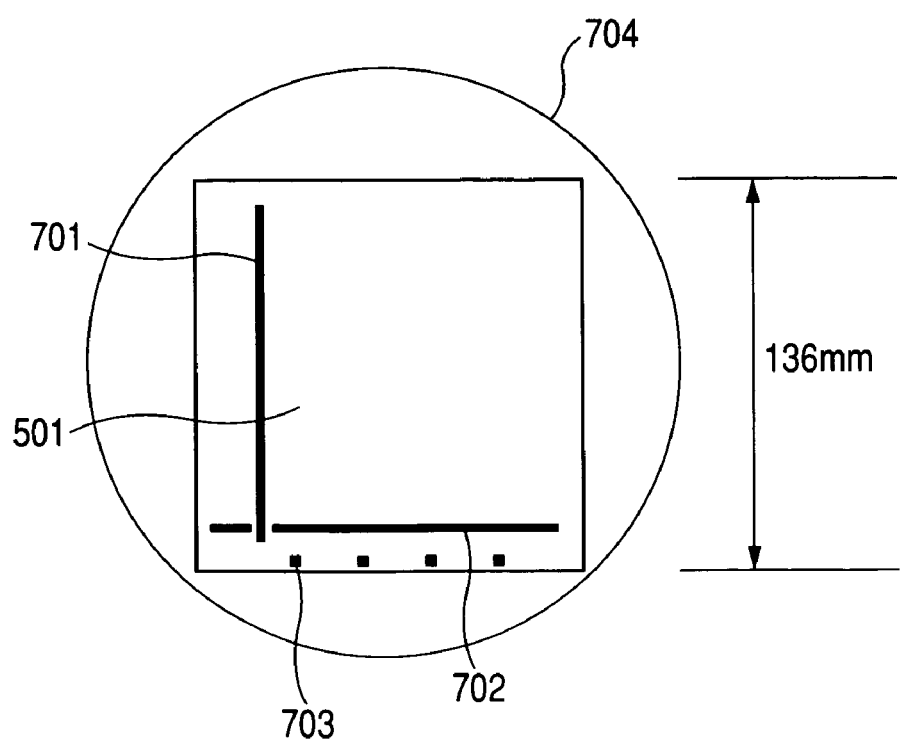
FIG. 7 is a plan view showing an image pick-up element in the first and fifth embodiments according to the invention and a wafer serving as a base of the element.

One image pick-up element of the X-ray image sensor is shown in FIG. 7. One sheet of a CMOS type image pick-up element substrate of (136 mm×136 mm) is formed by the CMOS process from a wafer 704 of 8 inches, which is a main stream at present. In the cone beam X-ray CT radiographing device for the medical examination, it is sufficient to set the pixel to a large size of about (500 μm×500 μm to 1 mm×1 mm). In the embodiment, the pixel size is set to (500 μm×500 μm). Although the structure in which the nine image pick-up elements are arranged is used in the embodiment, the size of image pick-up element in the invention can be arbitrarily selected, so that the number of image pick-up elements to be arranged is also properly variable. Preferably, the size and the number of image pick-up elements are determined in consideration of a yield of the image pick-up elements, a yield in the installing step, and the like. Reference numeral 701 denotes a vertical shift register; 702 a horizontal shift register; and 703 external terminals.

Figure 8:
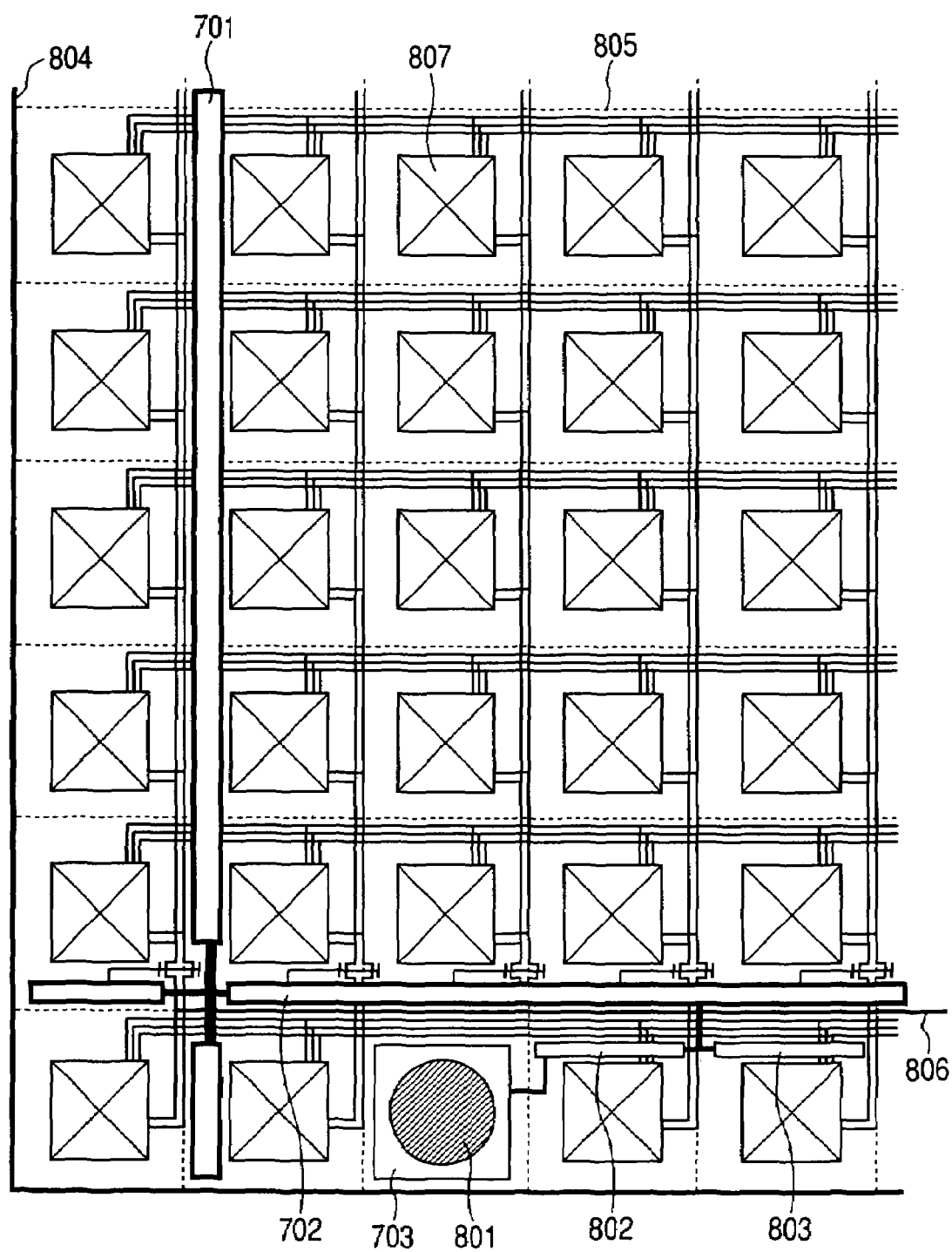
FIG. 8 is a plan view showing an array of pixels and an array of scanning circuits in an image pick-up element of the first embodiment according to the invention.

FIG. 8 shows a construction (plan view) of the image pick-up element of the embodiment. In the embodiment, the vertical shift register 701 and the horizontal shift register 702 are arranged in a valid region of the image pick-up element and a plurality of pixels 807 are two-dimensionally arranged in the vertical and horizontal directions in the image pick-up element. They are arranged so that one block of the shift registers for processing one line is enclosed in one pitch. By arranging those blocks, a series of vertical shift register blocks and a series of horizontal shift register blocks are formed. Those blocks are rectilinearly extended in the vertical and horizontal directions.

Further, it is assumed that at least photosensing regions of all pixels are set to the same area. In FIG. 8, the areas of the 1-pixel circuits among the cells are equal and the areas of the photosensing regions in the 1-pixel circuits among the cells are equal. Although it is desirable to equalize the areas of the photosensing regions with respect to all cells, there is a possibility that the area of the photosensing region in the cell in one line existing in an edge portion of the image pick-up element differs from that of the photosensing region in the cell existing in the circuit in order to assure a margin for slicing. A bump 801 is formed on the external terminal 703. A protective resistor 802 and a protective diode 803 to protect the internal circuit against static electricity are connected to the bump 801. The external terminal 703 is used to connect to the flexible board 603 as mentioned above.

A multiplexer is formed in the image pick-up element in order to quickly execute the operation of the image pick-up element. The signal is extracted from the image pick-up element to the outside through the external terminal 703. However, there is a large floating capacitance around the external terminal 703. Therefore, transmitting characteristics of the signal can be compensated by providing an amplifier for a front stage of the external terminal 703.

Figure 9:
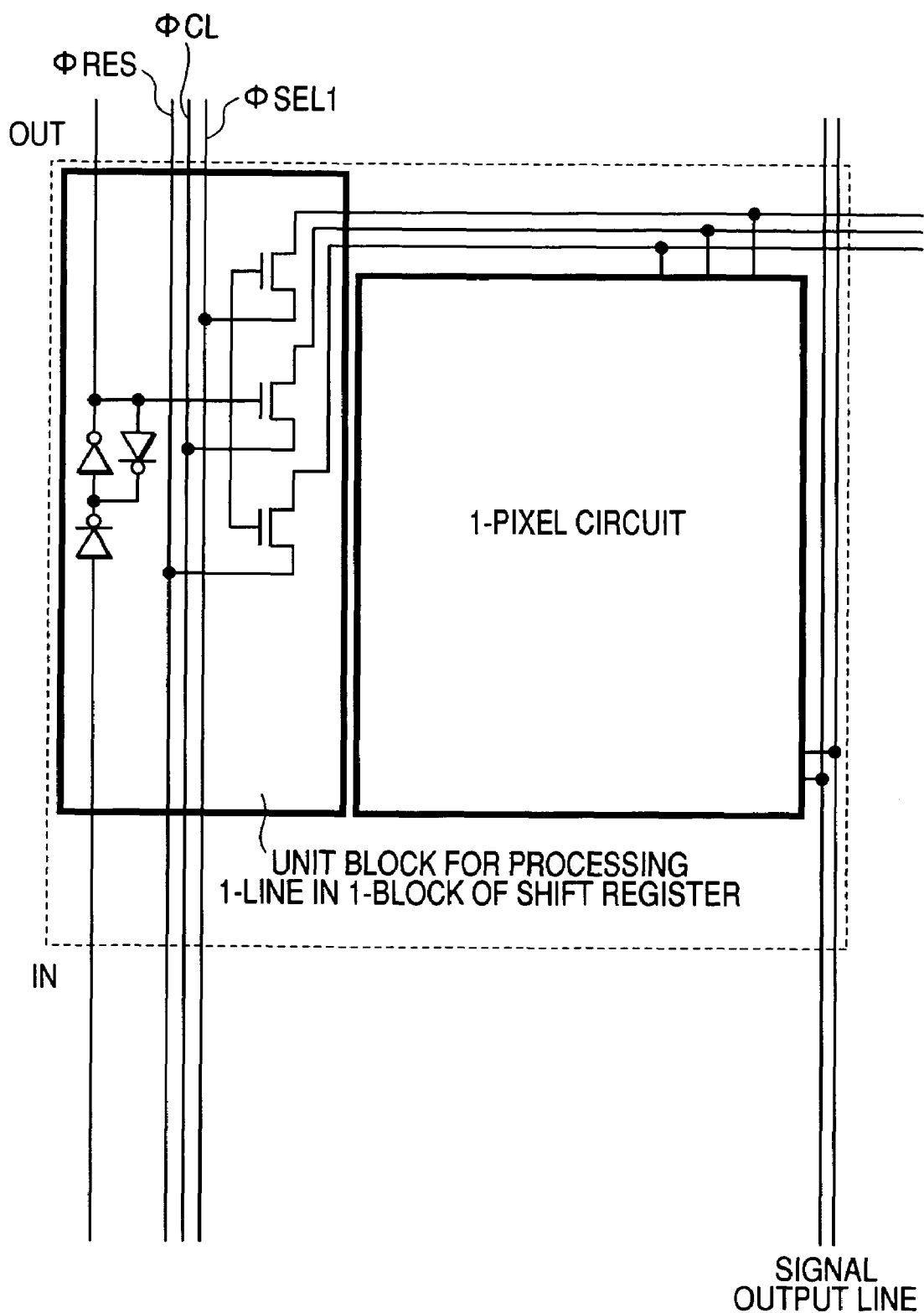
FIG. 9 is a diagram showing a relation between a 1-pixel circuit in the image pick-up element and a unit block of a shift register in the first embodiment according to the invention.
Figure 10:
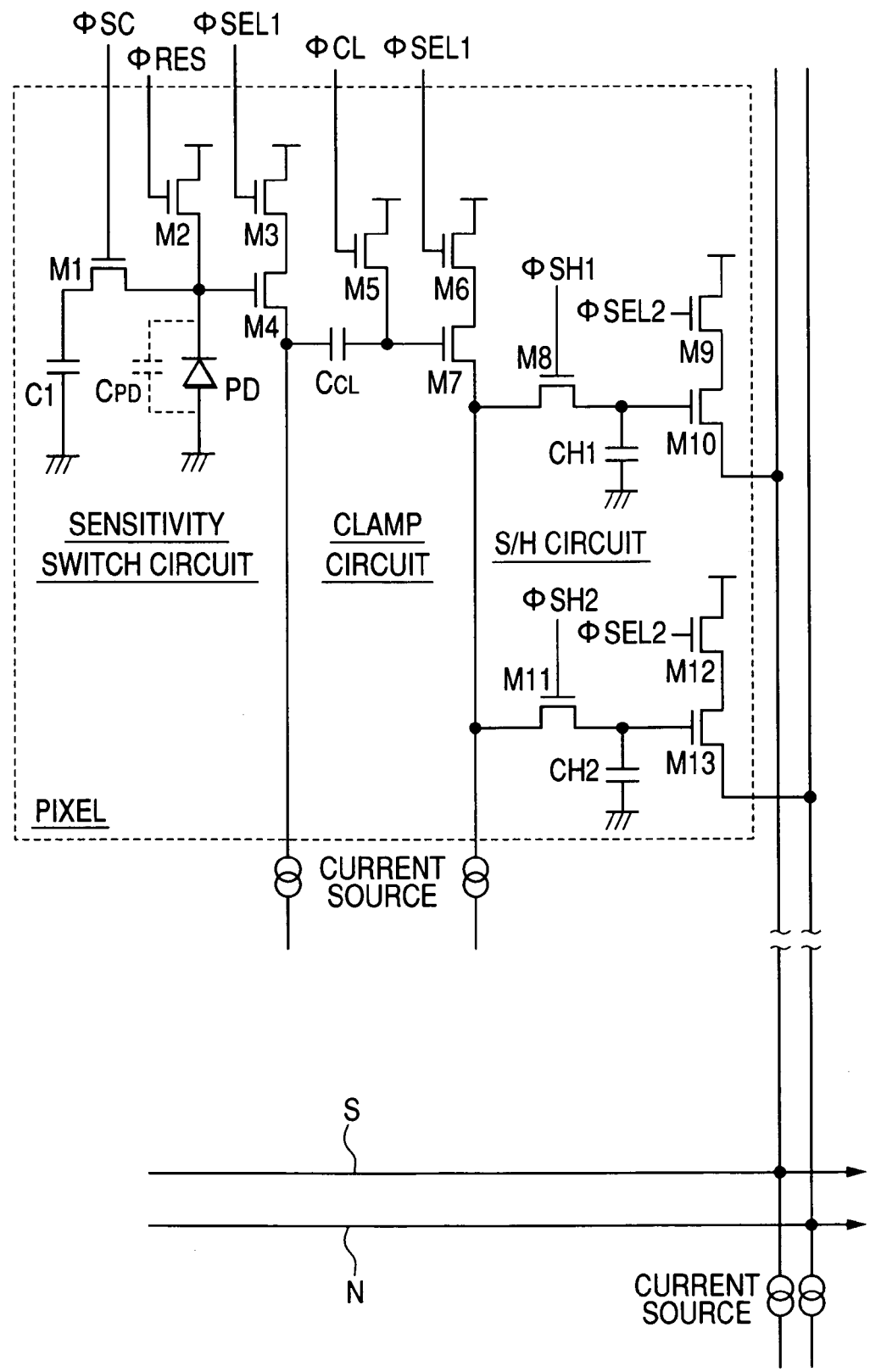
FIG. 10 is a circuit diagram of one pixel of the image pick-up element in the first embodiment according to the invention.

FIG. 9 shows the state where a unit block (unit to select and drive one row) of the vertical shift register is arranged in one region (one cell) together with a 1-pixel circuit. The 1-pixel circuit is shown in FIG. 10. An actual element layout is not reflected to the areas of the unit block and the pixel circuit because the diagram shows a schematic diagram. As a vertical shift register, a simple circuit constructed by a static type shift register and a transfer gate in order to form a reset signal φRES, a clamp signal φCL, and a selection signal φSEL1 is shown. Signal lines other than signal lines of the reset signal φRES, clamp signal φCL, and selection signal φSEL1 are omitted here.

They are driven by a signal from a clock signal line (not shown). The circuit construction of the shift register is not limited to that mentioned above but an arbitrary circuit construction can be used in accordance with various driving methods such as addition reading, decimation reading, and the like. However, it is assumed that the functional blocks are arranged in one cell together with the pixel circuit, the shift registers are arranged in the valid region, and the image pick-up elements of the whole valid region are realized as shown in the embodiment.

In place of the shift register, an n-to-$2^n$ decoder can be also used as a scanning circuit. In this case, by connecting an output of a counter which is sequentially incremented to an input of the decoder, it is possible to sequentially scan in a manner similar to the shift register. By inputting an address of a region where the operator wants to obtain an image into the input of the decoder, the image of an arbitrary region can be obtained by the random scan. A common processing circuit which is arranged in each region (cell) in the valid region denotes a circuit for batch-processing in common with a plurality of component elements such as final-signal output amplifier, serial/parallel conversion multiplexer, buffer, various gate circuits, and the like.

FIG. 10 shows a 1-pixel circuit. A kTC correction in a photoelectric converting unit is performed in the pixel. Further, by providing sensitivity switching means into the pixel, the sensitivity (dynamic range) is realized by mode switching. A capacitance of the photodiode PD is reduced as much as possible to raise the sensitivity. At this time, the dynamic range decreases. Therefore, a capacitor C1 is provided in parallel with the photodiode PD in order to assure the dynamic range.

M1 denotes a change-over switch to switch the sensitivity. A photodiode capacitor $C_{PD}$ to accumulate the charges is designed to the minimum capacitance so as to obtain the maximum sensitivity upon photographing. M2 denotes a reset MOS transistor (reset switch) to discharge the charges stored in the photodiode capacitor $C_{PD}$; M3 a selection MOS transistor (selection switch) to select a pixel amplifier 1; and M4 an amplification MOS transistor (pixel amplifier 1) functioning as a source follower. By forming those circuit elements for every pixel on the same wafer, a capacitance of a gate portion of M4 can be also reduced as much as possible and the sensitivity can be improved.

Hitherto, since the source follower is not suitable from a viewpoint of the dynamic range, it is not used in a signal amplifier for the CT. In the embodiment, however, by introducing the sensitivity switching in the photodiode portion, the source follower construction can be used. By constructing the source follower for every pixel, the sensitivity can be extremely improved and the X-ray image sensor panel suitable for the cone beam X-ray CT radiographing device can be realized. Further, since the circuit has the source follower for every pixel, non-destructive reading operation can be performed. Various data can be read out by the non-destructive reading function independent of the main reading operation. For example, it is also possible to provide a function for monitoring an amount of charges stored in the photodiode of every pixel, read them out to the outside in a non-destructive manner, and switch the sensitivity before the charge amount reaches a saturation amount.

A clamp circuit is provided at the post stage of the pixel amplifier 1. kTC noises which are generated in the photoelectric converting unit are removed by the clamp circuit. $C_{CL}$ denotes a clamp capacitor and M5 indicates a clamp switch. The noise removal can be executed by the following operation. By turning on the switch M5, an electrode of the clamp capacitor $C_{CL}$ existing on a pixel amplifier M7 side is set to a predetermined electric potential.

When the photodiode PD is reset by the reset switch M2 in this state, noise components are stored into the electrode of the clamp capacitor $C_{CL}$ existing on the amplification MOS transistor M4 (pixel amplifier 1) side. By storing the signal charges of the photodiode PD after the turn-on of the switch M5, the electrode potential of the clamp capacitor $C_{CL}$ existing on the amplification MOS transistor M4 (pixel amplifier 1) side fluctuates by an amount corresponding to the noise components removed from the signal (containing the noise components) of the photodiode. Also, in the amplification MOS transistor M7 (pixel amplifier 2) of the clamp capacitor $C_{CL}$, the electrode potential fluctuates by an amount corresponding to the removed noise components. The signal from which the noise components are removed is held in the clamp capacitor $C_{CL}$ as mentioned above.

A sampling and holding circuit (S/H circuit) is provided after the clamp circuit. M6 denotes a selection MOS transistor (selection switch) to select the pixel amplifier 2; M8 a sample MOS transistor switch constructing a sampling and holding circuit for storing a photosignal; CH1 a holding capacitor; M10 an amplification MOS transistor (pixel amplifier 3) functioning as a source follower; M9 a selection MOS transistor (selection switch) to select the pixel amplifier 3; M11 a sample MOS transistor switch constructing a sampling and holding circuit for storing a noise signal; CH2 a holding capacitor; M13 an amplification MOS transistor (pixel amplifier 4) functioning as a source follower; and M12 a selection MOS transistor (selection switch) to select the pixel amplifier 4.

Generally, in an amplifying type image pick-up element such as a CMOS type image pick-up element or the like, amplifying means (amplifier in the pixel) is provided in the element in order to improve a signal-to-noise ratio (S/N ratio) upon reading, thereby increasing a gain of the signal. In the image pick-up element of the embodiment, the source follower of the MOS transistor which is used as amplifying means is used. Generally, a threshold value Vth of the MOS transistor is liable to vary. Such a variation is peculiar to the design and manufacturing of the element and detrimental because it varies every pixel and every element. Particularly, in the large image pick-up element which is used in the embodiment, the variation in the element is liable to increase. In the case of using a plurality of image pick-up elements, the variation among the elements is large. Such a variation appears as a fixed output fluctuation, that is, what is called a fixed pattern noise (FPN) or an uneven background image.

Since a 1/f noise (flicker noise) or a thermal noise is liable to occur in the MOS transistor and it is a random noise, a random background image occurs. In the device design, assuming that a channel length of the MOS transistor is set to L and a channel width is set to W, since the thermal noise is proportional to $(L/W)^{1/2}$ and the 1/f noise is inversely proportional to $L \cdot W$, it is preferable to minimize the channel length L and increase the channel width W in order to reduce the noises of the MOS transistor. Particularly, if the channel width W of the source follower serving as an amplifier which becomes a large noise source is set to a large value, a parasitic capacitance between a gate and a drain increases, the gain is decreased, and the sensitivity deteriorates. Therefore, it is difficult to embody the MOS transistor.

In the embodiment, a PMOS transistor whose 1/f noise is essentially small is used at least as a source follower. Consequently, the noise can be reduced to a level of about 1/10 as compared with that of an NMOS transistor. Even if the X-ray which passed through the scintillator directly collides with the transistor, since X-ray durability of the PMOS transistor is higher than that of the NMOS transistor (an increase in leakage current and a fluctuation in threshold value Vth are smaller), the PMOS transistor is further preferable.

Since the threshold value Vth changes exponentially in dependence on a temperature, even if each source follower has a temperature difference of 1 degree or less during the photographing, it appears as a fluctuation of the output. In the case of the X-ray image sensor constructed by a plurality of image pick-up elements as in the embodiment, if temperature dependency differs every image pick-up element, such a small fluctuation also causes a correction error. In the case of the X-ray CT radiographing, if the correction error occurs even in one image pick-up element, a ring artifact which is very conspicuous on the image occurs and becomes a problem. Therefore, in the two source followers of the sampling and holding circuit, a layout structure in which the variation of the threshold value Vth is as small as possible as a layout is used as will be explained hereinafter, and further, a mechanism in which a temperature difference does not occur during the operation is used.

Therefore, there is used a structure in which the sampling and holding (S/H) circuit for the photosignal and the S/H circuit for the noise signal are provided in the pixel as mentioned above, the photosignal and the noise signal are stored independent of the exposure, and the signals are simultaneously outputted (the signals of two lines per column are outputted) from the S/H circuits.

As mentioned above, in the cone beam X-ray CT radiographing using the continuous X-ray, it is necessary to obtain each projection image by driving all of the display screens at the same timing and the same storage period. For this purpose, a structure in which a memory is provided in each pixel is used. One projection image signal at the same timing and the same storage period is stored into the memory in the pixel and, while the next projection image is obtained, the stored projection data can be read out at a high speed by the parallel reading operation. First, the S/H circuit functions as means (memory in the pixel) for storing the image signal independent of the exposure. The cone beam X-ray CT radiographing of a large area which could not be realized hitherto can be realized by the parallel reading operation of the image pick-up elements and those structures and functions.

Further, the circuit has a noise removing function. Since the photosignal and the noise signal are fetched into the S/H circuit from the pixel amplifier 1 at a very small time difference, the large 1/f noise of a low frequency can be ignored.

The thermal noise, 1/f noise, and FPN in the pixel amplifier are removed by using the circuit. The variation of the two S/H circuit elements is reduced as much as possible by the method whereby the capacitors are arranged at the closest positions in the pixel, the source followers of the outputs are arranged in a cross layout which is used in the ordinary MOS circuit layout, and the variation of the threshold value Vth is reduced as much as possible. As mentioned above, the S/H circuit of the embodiment functions as storing means of every pixel for the batch-exposure, also functions as noise removing means, and further functions to eliminate the output fluctuation among the image pick-up elements due to the temperature change.

It is a feature of the invention that the control of the timing for obtaining each projection image is made by using the angle signal which is outputted from the rotary encoder 103. The reading switch and the reset switch are driven by pulse signals formed by the storage period controller 208 on the basis of the angle signal from the rotary encoder 103.

The angle signal which is outputted from the rotary encoder 103 is sent to the storage period controller 208. A timing pulse for the batch-reset and an operation timing pulse for the batch-exposure are formed on the basis of this signal. Those operation timing and the operation timing of the S/H circuit are controlled and the projection image signal is stored and outputted for the storage period corresponding to the angle of one projection so that a time lag is not caused in each projection image. Thus, even if there is a rotational variation in the rotating plate, the projection image of the period corresponding to the rotational angle per projection which has accurately been determined can be obtained. The storage period is completely synchronized with the storage period of the signal storage type reference element 104 mentioned above.

Figure 11A:
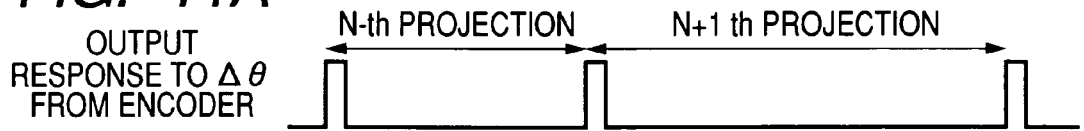
FIGS. 11A, 11B, 11C, 11D, 11E, 11F, 11G and 11H show a timing chart of a driving method in the first embodiment according to the invention.
Figure 11B:
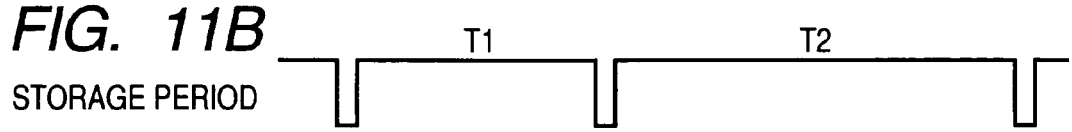
Figure 11C:
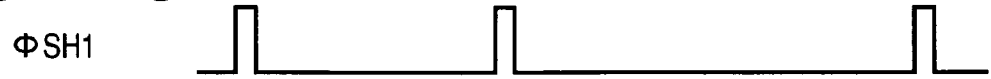
Figure 11D:
Figure 11E:
Figure 11F:
Figure 11G:
Figure 11H:
Figure 12:
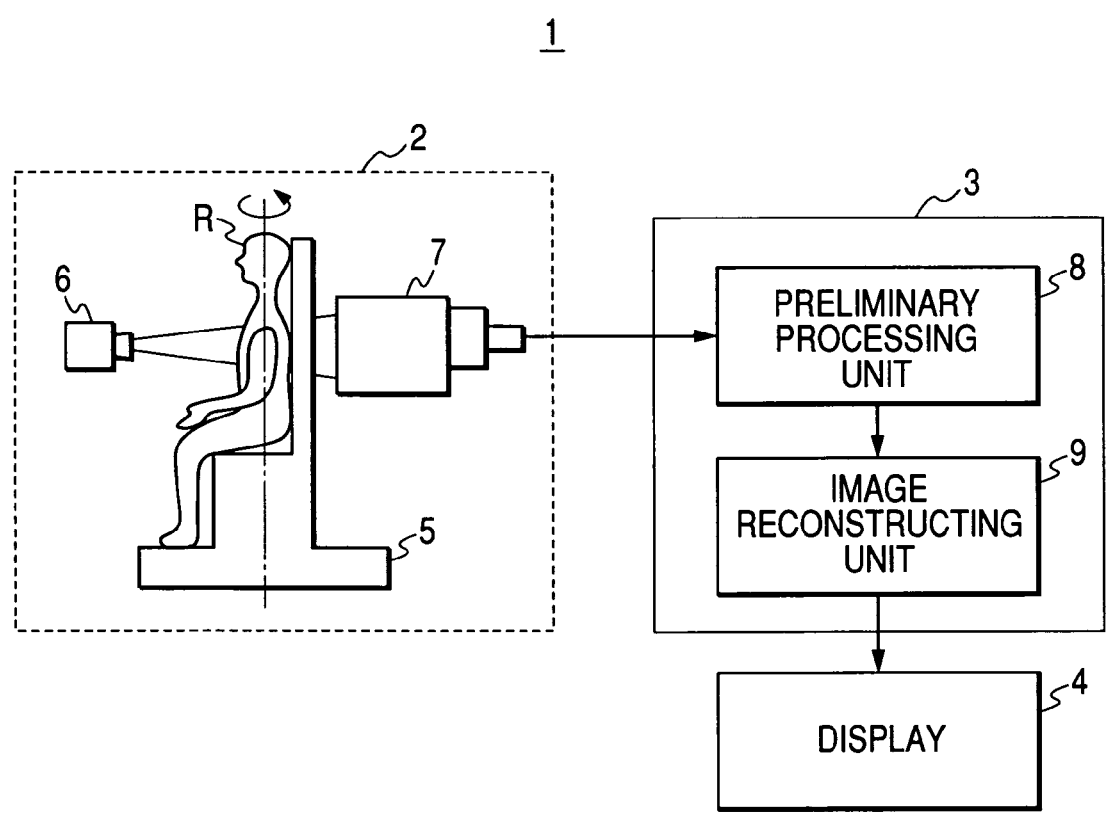
FIG. 12 is a conceptual diagram showing a construction of a conventional radiographing system.

FIGS. 11A-11H is a timing chart showing operation timing of the pixel portion in the embodiment. FIG. 11A shows the output response to $\Delta\theta$ of the encoder. FIG. 11B shows the storage period. FIG. 11C shows $\phi SH1$. FIG. 11D shows $\phi RES$. FIG. 11E shows $\phi CL$. FIG. 11F shows $\phi SH2$. FIG. 11G shows clocks. FIG. 11H shows the storage period of the signal storage type reference element.

The circuit operation will now be described with reference to FIG. 11. First, the photoelectric conversion is executed by the photodiode PD. The exposure is performed by the batch-exposure at the same timing and same period with respect to all of the pixels of each image pick-up element. Therefore, no time-dependent deviation of the image occurs among the image pick-up elements and among scanning lines.

First, as shown in FIG. 11A, the signal corresponding to the start angle of the N-th projection is sent from the rotary encoder 103 to the storage period controller 208.

As shown in FIG. 11C, by simultaneously setting the signal $\phi SH1$ to the high level and turning on the sample switch M8 in a lump by the storage period controller 208 with respect to all of the pixels, the photosignal which has been stored in the previous projection and from which the noises have been removed is transferred in a lump into the capacitor CH1 through the pixel amplifier 2 (M7).

As shown in FIG. 11D, by setting the signal $\phi RES$ to the high level and turning on the reset switch M2 in a lump with respect to all of the pixels, the photodiode capacitor $C_{PD}$ is reset. The signal storage corresponding to the N-th projection starts from the end point of the resetting operation. Since the signal $\phi SH1$ is controlled by the storage period controller 208 and the other signals are determined in response to $\phi SH1$, the signal storage in the photodiode is controlled in every projection.

At the same time, as shown in FIG. 11E, by setting the signal $\phi CL$ to the high level and turning on the selection switch M3 of the pixel amplifier 3 and the clamp switch M5, the clamp capacitor $C_{CL}$ is set to the reference voltage.

At the same time, as shown in FIG. 11F, by setting the signal $\phi SH2$ to the high level and turning on the selection switch M6 of the pixel amplifier 6 and the sample switch M11 in a lump with respect to all of the pixels, the noise signal when the circuit is set to a reference voltage is transferred to the capacitor CH2. Subsequently, by setting the signal $\phi SH2$ to the low level, the transfer and holding of the photosignal and the noise signal into the S/H circuit are finished.

Subsequently, by setting the signal $\phi SEL2$ to the high level every row and turning on the selection switches M9 and M12 by the signal which is inputted to the shift register VSR, the source follower circuit constructed by a load current source and pixel amplifiers 3 and 4 (M10 and M13) is made operative. Thus, the photosignal and the noise signal held in the holding capacitors CH1 and CH2 are simultaneously transferred to a photosignal output line and a noise signal output line through the pixel amplifiers 3 and 4.

As shown in FIG. 11B, a storage period T1 of the X-ray image sensor panel 101 is started by the above operation. The storage period is controlled for every frame by the encoder output as mentioned above.

With respect to the storage period of the signal storage type reference element 104, as shown in FIG. 11H, the switches SW1 and SW2 are similarly controlled by the storage period controller 208 and the signal of each projection is stored and outputted for the same storage period as that of the X-ray image sensor panel 101.

By repeating the above operation, the storage period of the X-ray image sensor panel 101 according to each projection and the storage period of the signal storage type reference element 104 are controlled by the encoder output.

A collecting procedure of the projection images of one rotation of the object in the object rotating type cone beam X-ray CT radiographing device of the embodiment will now be described. First, the observer fixes the object 107 to a holding device. Subsequently, when the observer instructs to start the measurement from an operation panel (not shown), the measurement of the projection image (projection data) is started by a control signal outputted from the radiographic control device 105 and the rotating plate 102 starts the rotation. At this time, the rotational angle signal is outputted from the rotary encoder 103 to the radiographic control device 105.

When it is detected that the rotational angle of the rotating device 102 has reached a predetermined angle, the radiographic control device 105 allows the X-ray generator 109 to immediately radiate the continuous X-ray. In association with the radiation of the X-ray from the X-ray generator 109, the radiographic control device 105 obtains the production image of the object 107 by controlling the X-ray image sensor panel 101. The production image is outputted as digital production data to the radiographic control device 105. The radiographic control device 105 collects the production image photographed by the X-ray image sensor panel 101 together with the rotational angle of the rotating device 102, that is, projection angle, stores them into the image data memory 203, and subsequently executes such an operation every predetermined angle, thereby finishing the photographing of the production images of one rotation.

After the photographing (collection) of the production images of the whole circumference is finished, the radiographic control device 105 finishes the rotation of the rotating device 102. In the image processing unit 202, the following preliminary processes are executed to the production images stored in the image data memory 203 by using the correction data which has already been stored in the correction data memory 204. That is, the gamma correction, image distortion correction, logarithm conversion, sensitivity variation correction of the X-ray image sensor panel, and the like are executed to each production image. Further, a 3-dimensional X-ray distribution image is reconstructed on the basis of the production images. Moreover, the image process such as well-known volume rendering process, maximum value projecting process, or the like is executed to the 3-dimensional X-ray distribution image. A 3-dimensional X-ray image as a 3-dimensional-like 2-dimensional is formed from the 3-dimensional X-ray distribution image. The 3-dimensional X-ray image is displayed onto the display screen of the display 106.

In the embodiment, by arranging the photosensing regions of a uniform size in each image pick-up element and among the image pick-up elements so that the centers of gravity are arranged at an equal pitch, even if the shift registers and the like are arranged in the valid region, a sensitivity variation and a variation of the centers of gravity of the photosensing regions do not occur among the image pick-up elements and in the image pick-up element. Thus, even in the construction in which a plurality of image pick-up elements are adhered, the image which is substantially seamless can be obtained. Since no dead spaces are caused around the image pick-up element, the whole surface of the image pick-up element becomes the valid region.

By arranging the image pick-up elements without substantially causing any gap, the image pick-up device of a large area can be formed. Further, by using such a circuit construction as mentioned above, the image of a large area which is substantially seamless with respect to the time and space can be obtained. Since the size of pixel is sufficiently large, even if the shift register is arranged in the valid pixel region or even if the circuit such as a sampling and holding circuit is arranged in the pixel, a sufficiently large numerical aperture can be realized. Therefore, no problem occurs. Further, since the structure in which the signals are read out from the image pick-up elements in parallel is used, they can be read out at a high speed.

In the embodiment, since the shift register is arranged in the valid region, the X-ray which passed through the scintillator 602 directly collides with the shift register. However, by using the static shift register as a shift register, an influence by the X-ray is not exercised. The shift register circuit is used to sequentially transfer the pulse signals. That is, since the static type shift register is relatively difficult to be influenced by the X-ray in principle, it can be used at a place where the X-ray directly collides with it. Therefore, by using the static type shift register, the image pick-up device in which an X-ray damage and an error are small and the reliability is improved can be realized.

Further, since the CMOS type image pick-up element is used as an image pick-up element in the embodiment, electric power consumption is small and it is suitable to the case of constructing the image pick-up device of a large area. By the sampling and holding circuit provided for each pixel, the whole surface batch-exposure, the FPN noise removal, and the reduction in artifact due to the temperature change can be realized. It is possible to realize the X-ray image sensor panel of a large area in which the photographing of a high speed exceeding 200 frames/sec can be performed, a high sensitivity similar to that of the radioscopic photographing is obtained, and the whole lung field of the human body can be CT radiographed. Further, the artifact due to the variation in rotational angle can be eliminated by the whole surface batch-exposure and the control of the storage period of each projection.

Second Embodiment

According to the second embodiment, an ionization dosimeter is used as a signal storage type reference element. Generally, the ionization dosimeter (area dosimeter) is used as a measuring instrument which is attached to an X-ray radioscopic device and measures radiation exposure of the patient at the time of the radioscopic operation. The area dosimeter is attached to a movable diaphragm portion of the X-ray generator. Component elements other than the area dosimeter are similar to those in the first embodiment.

In the second embodiment, the area dosimeter is set so as to cover the front surface of the movable diaphragm of the X-ray generator. A value which is measured by the area dosimeter is a total dosage of the X-ray which is generated from a range limited by the movable diaphragm in the X-ray which is generated from the X-ray generator. In the first embodiment, the signal storage type reference element is set to a position where it does not become a shadow on the object. Since the area dosimeter transmits most of the X-ray, even if it is set so as to cover the front surface of the movable diaphragm of the X-ray generator, no problem will occur. Thus, since (an average of) the whole X-ray which is radiated to the object can be monitored, in the case of correcting the dosage of the projection image by using such a value, the precision is improved more than that in the case of the first embodiment.

The invention is not limited to the area dosimeter but another arbitrary X-ray radioscopic type sensor can be also used in a similar manner. A conventional flat panel detector using a-Si on a glass substrate can be also used. That is, the flat panel detector divided into a plurality of pixels is set so as to cover the front surface of the movable diaphragm. As for the pixel division in this instance, since it is sufficient to divide the range limited by the movable diaphragm into, for example, nine ranges, the conventional flat panel detector can be also used for the X-ray CT radiographing. In the case of correcting the dosage of the projection image by using the X-ray dosage values measured by dividing the range into the nine ranges, it is possible to make the correction which is further optimized.

Third Embodiment

Figure 4:
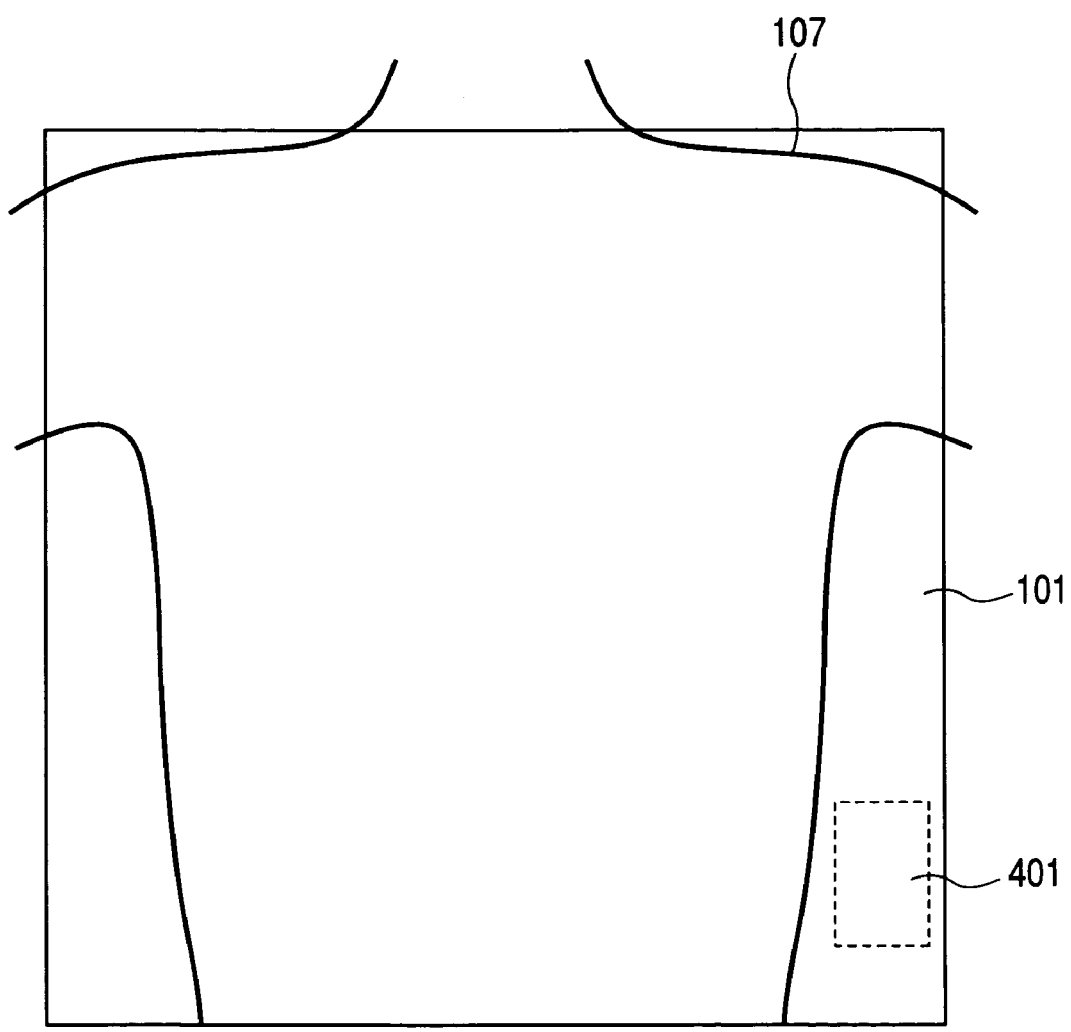
FIG. 4 is a diagram for explaining the third embodiment of the invention.

According to the third embodiment, a part of the X-ray image sensor panel is used as a reference element. The operation of the X-ray image sensor panel 101 is substantially the same as that of the first embodiment. As shown in FIG. 4, an X-ray radioscopic image includes portions without a projection image of the object, that is, blank portions. A region 401 surrounded by a broken line among the blank portions is used as a reference signal detecting portion. This region is determined by radiating the very weak X-ray prior to the main scanning and detecting the blank portions. After the reference signal detecting portion is determined, a collimator for removing scattered lines from the object is set to the relevant location of the X-ray image sensor panel. A grid can be also used in common. In the embodiment, since another reference detecting element is unnecessary, the image of the object and the reference signal can be simultaneously obtained as one image data. Thus, the system is simplified.

Fourth Embodiment

The fourth embodiment will be described with reference to FIG. 2. This embodiment relates to a correcting method.

The obtainment of the image data of the object is substantially the same as that of the first embodiment. In the fourth embodiment, further, the storage period control pulse formed by the storage period controller 208 is monitored by using the storage period calculation counter 209 in FIG. 2 upon photographing of the object and the number of clocks (FIG. 11G) for such a period is counted, thereby obtaining T1 and T2 (FIG. 11B). They are obtained with respect to all of the projection images and stored into storing means. The data from the reference element is also stored.

Usually, the sensitivity of the X-ray image sensor panel is measured prior to photographing the object in the state where there is no object. At this time, the storage period is set to a predetermined value (5 msec) and 1000 data is obtained because it is not concerned with the rotating device 102. The measurement comprises obtaining dark image (containing the FPN) data of the X-ray image sensor panel 101 which is obtained in the state where no X-ray is radiated and obtaining white image data when the X-ray is radiated. To correct the X-ray radioscopic image of the object, average data of the dark image data and the white image data is prepared.

Although the data of 5 msec has to be used as it is for the correction hitherto, in the embodiment, the average data is corrected by the storage period data stored every projection and further corrected by using the stored signal data of the reference element. White image correction and black image correction are made every projection by using the average value which was corrected as mentioned above. Thus, even if there are a fluctuation and a rotational variation of the X-ray source, the image of the object can be accurately corrected. Consequently, a tomogram image of high picture quality without an artifact can be obtained. Other constructions are similar to those in the first embodiment.

Fifth Embodiment

Figure 13:
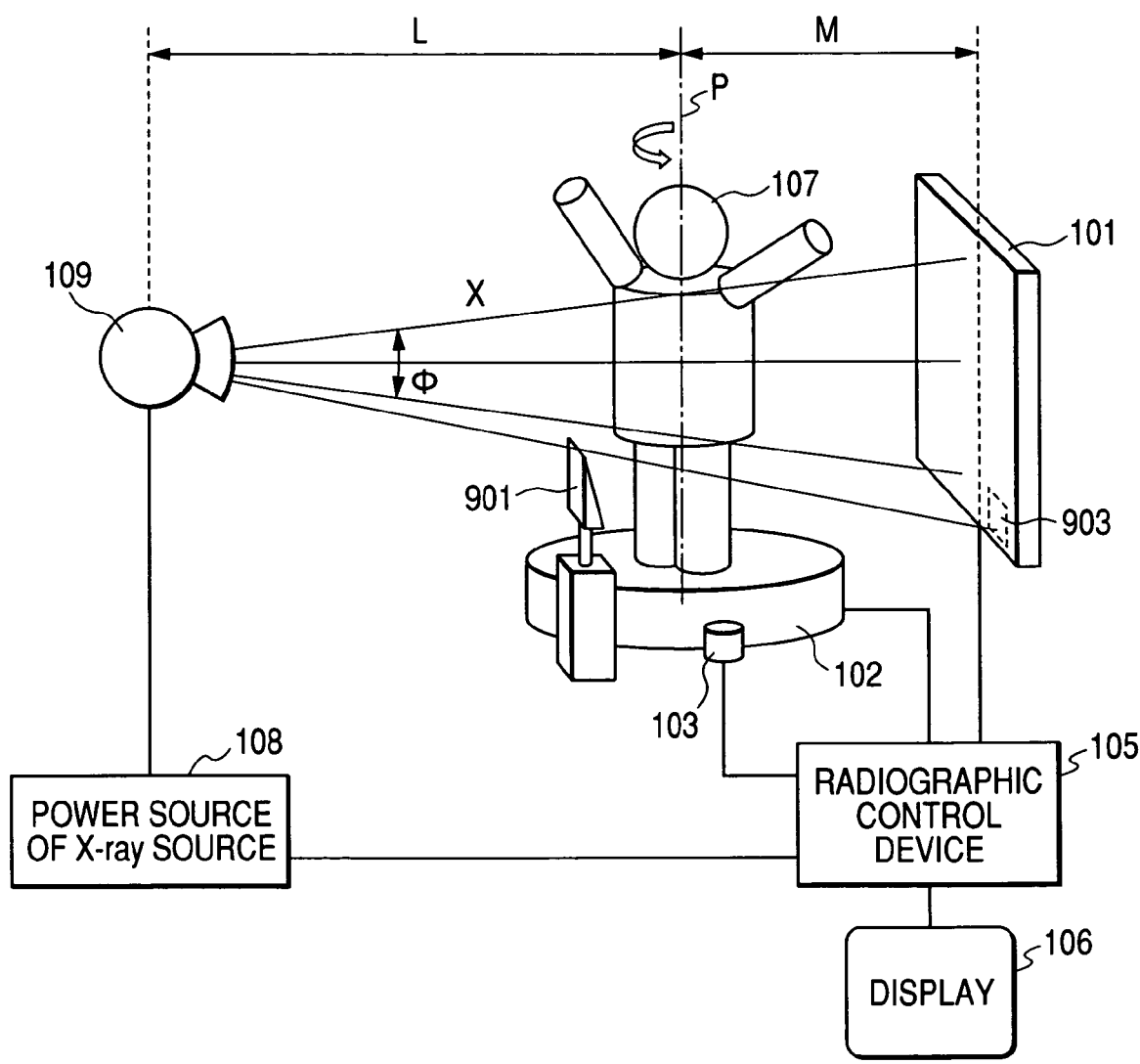
FIG. 13 is a schematic diagram showing the fifth embodiment of an object rotating type cone beam radiation CT radiographing device according to the invention.
Figure 14:
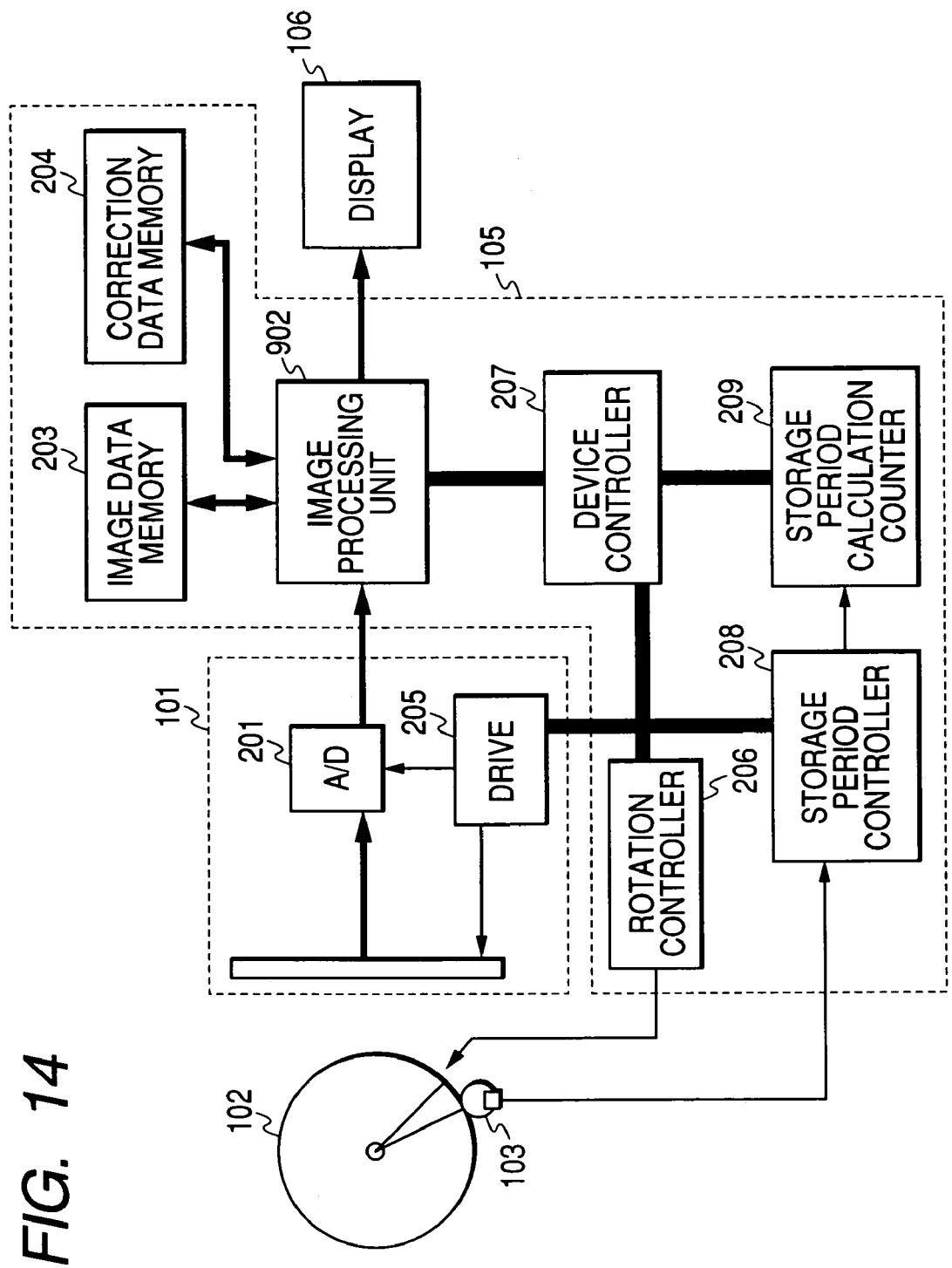
FIG. 14 is a system block diagram showing the fifth embodiment of the object rotating type cone beam radiation CT radiographing device according to the invention.

FIG. 13 is a diagram for explaining a schematic construction of the fifth embodiment of an object rotating type cone beam radiation CT radiographing device according to the invention. FIG. 14 is a block diagram of its system. In the diagram, reference numeral 109 denotes the X-ray generator (X-ray source); 108 the power source for the X-ray source; 901 an edge block; X the radiated continuous X-ray; 107 the object; 102 the rotating device (rotating plate); P the rotary axis of the rotating device; 103 the rotary encoder; 101 the X-ray image sensor panel; 105 the radiographic control device; and 106 the display. Although the X-ray is used as a radiation in the embodiment, another radiation such as α-ray, β-ray, γ-ray, or the like can be used. This is true of all embodiments.

The device for the general photographing is used as an X-ray generator 109 and it is used in the continuous X-ray mode. The radiographic control device 105 sets a lamp voltage, a lamp current, and radiation time and controls only the start and stop of the radiation. A geometrical layout of the X-ray generator 109, rotating plate 102, and X-ray image sensor panel 101 is accurately set. That is, it is set so that a perpendicular drawn from an X-ray focal point to the X-ray image sensor panel 101 passes through the rotary axis. The distance between the X-ray focal point and the rotary axis P of the rotating plate 102 is set to L and the distance between the rotary axis P and the X-ray image sensor panel 101 is set to M. By changing the values of L and M, the enlargement ratio of the projection image and the cone angle Φ of the cone beam can be set. The rotating plate 102 and the X-ray image sensor panel 101 are movable and, after their geometrical layout is determined, they are fixed at the locations of the layout.

The rotating device 102 is a device for continuously rotating the rotating portion on the basis of the rotation control signal from the radiographic control device 105. The holding device (not shown) to hold the object during the rotation is attached to the rotating portion. The rotary encoder 103 to measure the rotational angle of the rotating device 102 and output it to the radiographic control device 105 is further provided. In the case where the object is photographed by the full scan during one rotation of 360° by 1000 projections, the rotary encoder generates the signal every angle of 0.36° per projection.

As shown in FIG. 14, the radiographic control device 105 includes: the image data memory 203 for storing the projection image data outputted from the X-ray image sensor panel 101; the correction data memory 204 for storing the correction data; an image processing unit 902; the device controller 207; the storage period controller 208; the storage period calculation counter 209; and the rotation controller (rotating device controller) 206. The X-ray image sensor panel 101 includes the A/D converter 201 and the drive 205.

The radiographic control device 105 controls the X-ray radiation from the X-ray generator 109 on the basis of the photographing conditions inputted from the observer, controls the visual field mode of the X-ray image sensor panel 101, and controls the number of pixels and the frame rate. The radiographic control device 105 also controls the storage period of each of the edge block 901 and the X-ray image sensor panel 101 by the storage period controller 208 on the basis of the signal from the rotary encoder 103.

The image processing unit 902 executes: the preliminary processes such as gamma correction, image distortion correction, logarithm conversion, sensitivity variation correction of the X-ray image sensor panel 101, and the like; the reconstruction for forming the 3-dimensional X-ray distribution image as 3-dimensional X-ray absorption coefficient distribution of the object 107 on the basis of the projection image (projection data) after the preliminary processes; and the image process such as well-known volume rendering process, maximum value projecting process, or the like which is executed to the 3-dimensional X-ray distribution image. The image processing unit 902 forms an X-ray tomogram image or a 3-dimensional X-ray image as a 3-dimensional-like 2-dimensional image from the 3-dimensional X-ray distribution image.

In the object rotating type cone beam X-ray CT radiographing device, if the object is rotated by 360° per rotation for 5 seconds and photographed by the full scan by 1000 projections, images are read out for 5 msec per projection (at a speed of 200 frames/sec) and it is, therefore, difficult to pulse-drive the X-ray source. Particularly, in the case of using the X-ray source for the general radiographing, it is difficult to radiate the stable pulse X-ray because a leading/trailing response speed of the lamp current is low. In the embodiment, therefore, the construction using the continuous X-ray is used. In the radiographing using the cone beam X-ray, it is necessary to obtain images without a time lag in the whole region for 5 msec.

In the embodiment, the edge block 901 to detect the movement of the focal point (hereinafter, referred to as focus movement) of the X-ray source 109 is arranged between the X-ray source 109 and the X-ray image sensor panel 101. It is set in a position where the X-ray which passes through the object 107 on the rotating plate 102 is not obstructed. The projection of the edge block 901 is detected in an edge detecting region 903 of the X-ray image sensor panel 101. The edge detecting region is not a special region but a virtual region of the X-ray image sensor panel 101 and can be freely set in accordance with a positional relation among the X-ray source 109, the edge block 901, and the X-ray image sensor panel 101.

Although only the rotational axial direction is presumed as a moving direction of the focal point of the X-ray in the embodiment, in the case of also detecting the movement in the horizontal direction, it is sufficient to devise a shape of the edge. That is, it is sufficient to form a spherical or conical edge shape by using tungsten, lead, or the like having a high contrast against the X-ray.

Figure 16A:
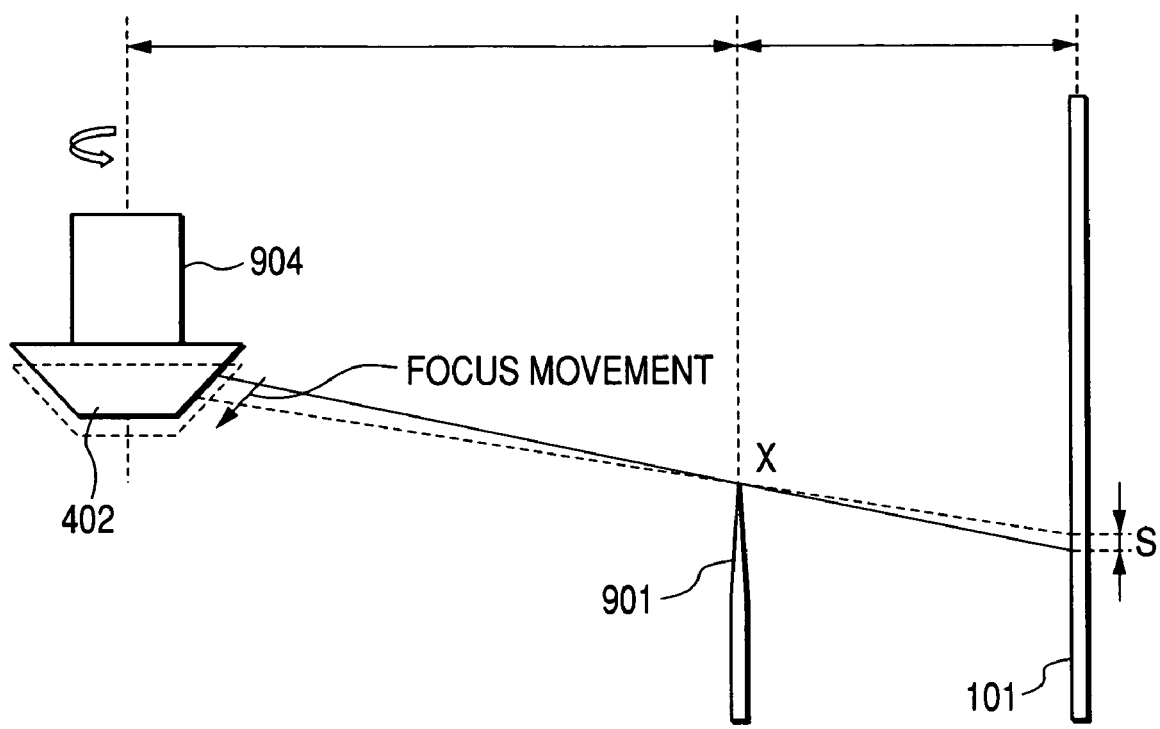
FIGS. 16A and 16B are diagrams for explaining focus movement detection according to the fifth embodiment of the invention. In particular

An influence of the focus movement will be described with reference to FIG. 16A. When the radiographing is started and a rotational anode 402 is heated, a thermal expansion occurs as shown by a broken line in the diagram. Thus, the focal point with which the electron beam collides is moved as shown in FIG. 16A. A projection image which is formed on the X-ray image sensor panel 101 when the X-ray emitted from the focal point collides with the edge of the edge block 901 is moved as shown in the diagram in association with the focus movement. Reference numeral 904 denotes a rotary shaft. In the embodiment, a structure and a method for accurately detecting an amount S of such movement are provided.

Figure 16B:
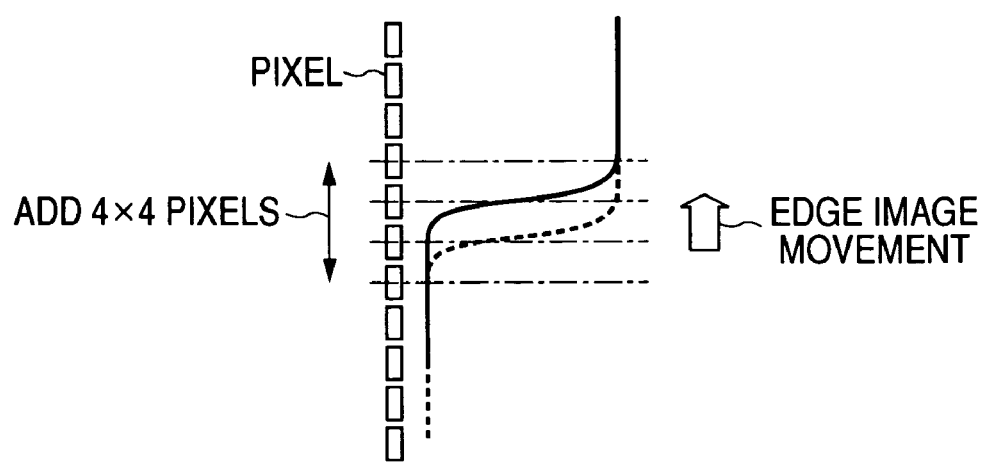

FIG. 16B illustrates a principle for accurately detecting the movement amount S on the X-ray image sensor panel 1001. In the case of obtaining a CT image, resolution for the whole display screen of 4×4 pixels is used. However, according to this resolution, it is difficult to precisely detect the movement of the edge portion. Therefore, only the edge portion is detected at resolution of 1×1 pixel. In the embodiment, the detection of the focus movement which does not exert an adverse influence on the obtainment of the CT image is realized.

In the embodiment, to precisely detect the movement of the edge portion of the X-ray source, the X-ray image sensor panel 101 having the following structure and driving method as will be explained hereinbelow is used. FIG. 5 shows an X-ray image sensor panel of a large area of (408 mm×408 mm) which is realized by two-dimensionally adhering the nine CMOS-type image pick-up elements 501 each having a size of (136 mm×136 mm) onto one base plate. Since the CMOS-type image pick-up elements are used, the charges stored for the common time can be read out from all of the elements at a high S/N ratio.

The image pick-up element mentioned in the invention denotes an image pick-up element panel on which a plurality of pixels are two-dimensionally arranged. The whole surface of the CMOS image pick-up element panel 501 is a pixel area as will be explained hereinafter. By adhering a plurality of image pick-up element panels onto the base plate, the image pick-up device of a large area which can obtain a seamless image can be realized. There is no limitation in its size in principle. If a desired image pick-up area can be formed by one image pick-up element panel, naturally, one image pick-up element can be also used.

FIG. 6 shows a cross sectional view taken along the line 6-6 in FIG. 5. The scintillator 602 is made of $Gd_2O_2S$ CsI, or the like using europium, terbium, or the like as a deactivator. The X-ray collides with the scintillator 602, is converted into the visible light, and is detected by the image pick-up elements. It is preferable to select the scintillator 602 so that its light-emitting wavelength is adapted to the sensitivity of the image pick-up element. The external processing board 605 is a board having a circuit for supplying a power source, clocks, and the like of the image pick-up elements, extracting the signals from the image pick-up elements, and processing them. The flexible board 603 is used to electrically connect each image pick-up element to the external processing board.

The nine image pick-up elements 501 are adhered onto the base plate 604 so that no gaps are substantially formed among the image pick-up elements. The wording "no gaps are substantially formed" denotes that no pixel defects occur in the joints and a dropout among the image pick-up elements does not occur in the image which is formed by the nine image pick-up elements. The input of the clocks, power source, and the like of the image pick-up element and the output of the signal from the image pick-up element are executed with the external processing board 605 arranged on the back side of the image pick-up element through the flexible board 603 connected to the external terminal 703 (refer to FIG. 7) in the edge portion of the image pick-up element.

Since the thickness of flexible board 603 is thin enough for the size, even if the X-ray is passed through the gap between the image pick-up elements, no defects on the image occur. The output signals from the image pick-up elements are read out in parallel. The high-quality image which is seamless with respect to the time and space and in which there is no time lag every projection can be obtained at a high speed of 200 frames/sec or more by the batch-exposure, which will be explained hereinafter, and the parallel reading operations of the image pick-up elements.

One image pick-up element constructing the X-ray image sensor is shown in FIG. 7. One sheet of the CMOS type image pick-up element substrate 501 of (136 mm×136 mm) is formed by the CMOS process from the wafer 704 of 8 inches which is a main stream at present. In X-ray CT radiographing device for the medical examination, it is sufficient to set the pixel to a large size of about (500 μm×500 μm to 1 mm×1 mm). In the embodiment, the pixel size is set to (160 μm×160 μm) smaller than the pixel size necessary for the diagnosis.

There are provided a structure and a reading method, in which a switch to change the resolution is provided for each pixel, data for the diagnosis can be outputted at resolution of (4×4) pixels, that is, (640 μm×640 μm), and a detection signal of the focus movement of the X-ray source can be outputted at resolution of (160 μm×160 μm). Reference numeral 701 denotes the vertical shift register; 702 the horizontal shift register; and 703 the external terminals.

Figure 17:
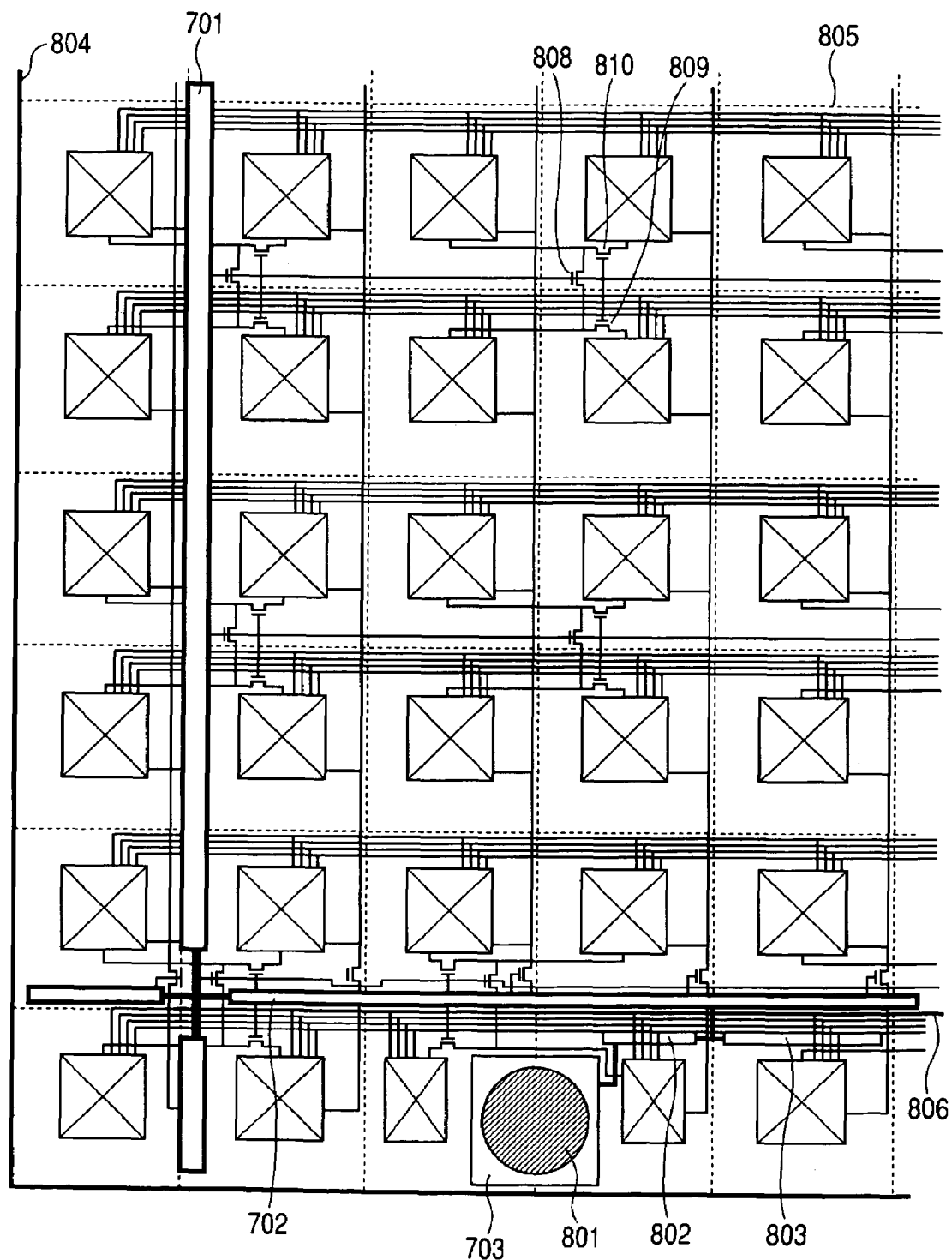
FIG. 17 is a plan view showing an array of pixels and an array of scanning circuits in the fifth embodiment of the invention.

FIG. 17 is a schematic diagram showing a construction of the image pick-up element of the embodiment. In the embodiment, the vertical shift register 701 and the horizontal shift register 702 are arranged in the valid region of the image pick-up element. A plurality of pixels are 2-dimensionally arranged in the vertical and horizontal directions in the image pick-up element. They are arranged so that one block of the shift registers for processing one line is enclosed in one pitch. By arranging those blocks, a series of vertical shift register blocks and a series of horizontal shift register blocks are formed.

Those blocks are rectilinearly extended in the vertical and horizontal directions. Reference numeral 808 denotes an ADD switch SW11 for adding the pixels; 809 an ADD switch SW10 for adding the pixels; and 810 an ADD switch SW12 for adding the pixels. In FIG. 17, only a layout of a switch for the photosignal in the case of adding (2×2) pixels is shown for simplicity of explanation. This is true of a switch for the noise signal. This idea is true of the addition of (4×4) pixels in the embodiment. A part of wirings and the like are also omitted.

Further, it is assumed that at least the photosensing regions have the same area with respect to all of the pixels. In FIG. 17, the areas of the 1-pixel circuits among the cells are equal and the areas of the photosensing regions in the 1-pixel circuits among the cells are equal. Although it is preferable to equalize the areas of the photosensing regions of all of the cells, there is a possibility that the area of the photosensing region in the cell in one line existing in the edge portion of the image pick-up element differs from that of the photosensing region in the cell existing in the circuit in order to assure the margin for slicing. In FIG. 17, the bump 801 is formed on the external terminal 703. The protective resistor 802 and the protective diode 803 to protect the internal circuit against static electricity are connected to the bump 801. The external terminal is used to connect to the flexible board 603 as mentioned above. Reference numeral 805 denotes a cell boundary on the layout and 806 indicates a signal line.

Figure 18:
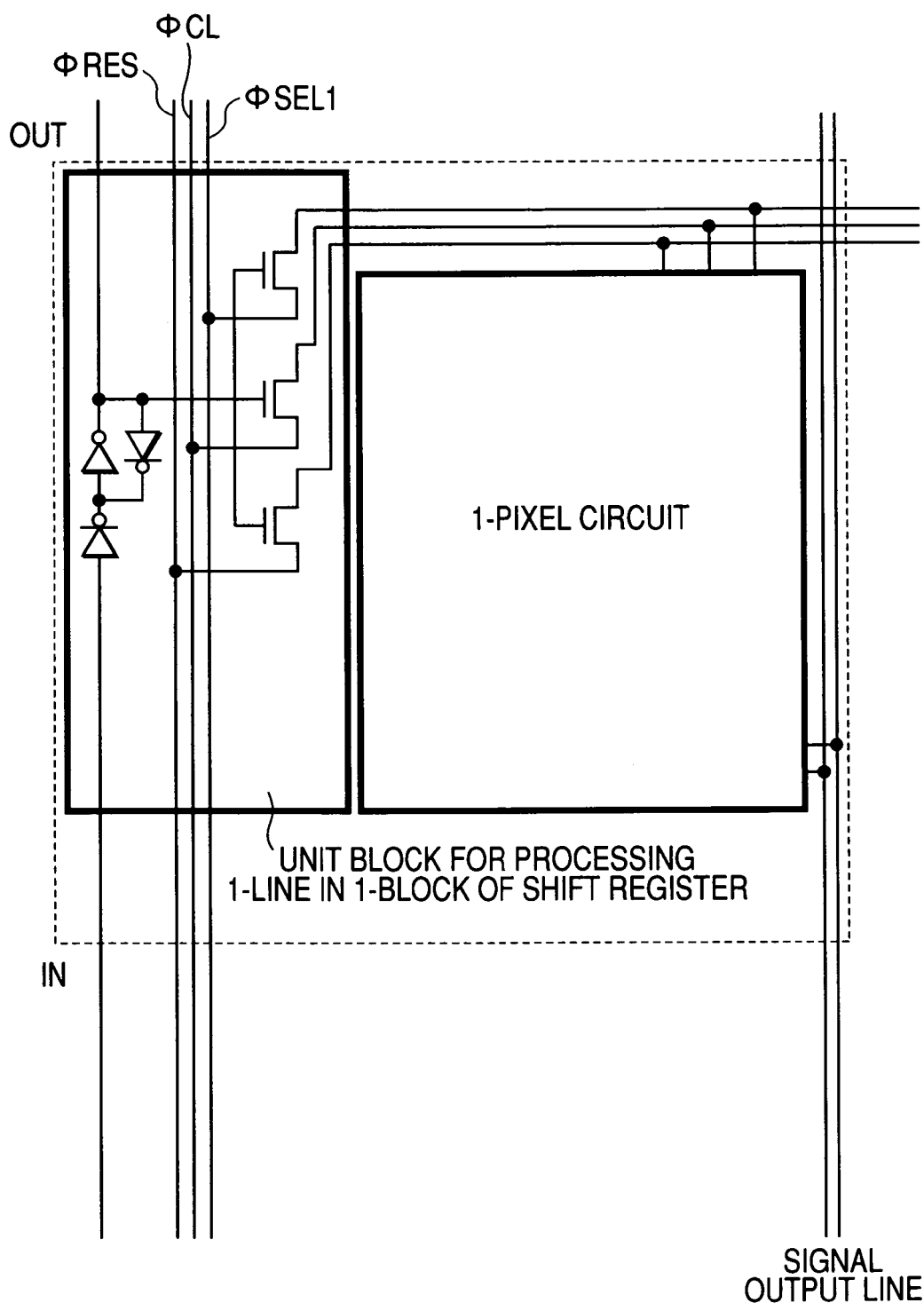
FIG. 18 is a diagram showing a relation between a 1-pixel circuit in the image pick-up element and a unit block of a shift register according to the fifth embodiment of the invention.
Figure 19:
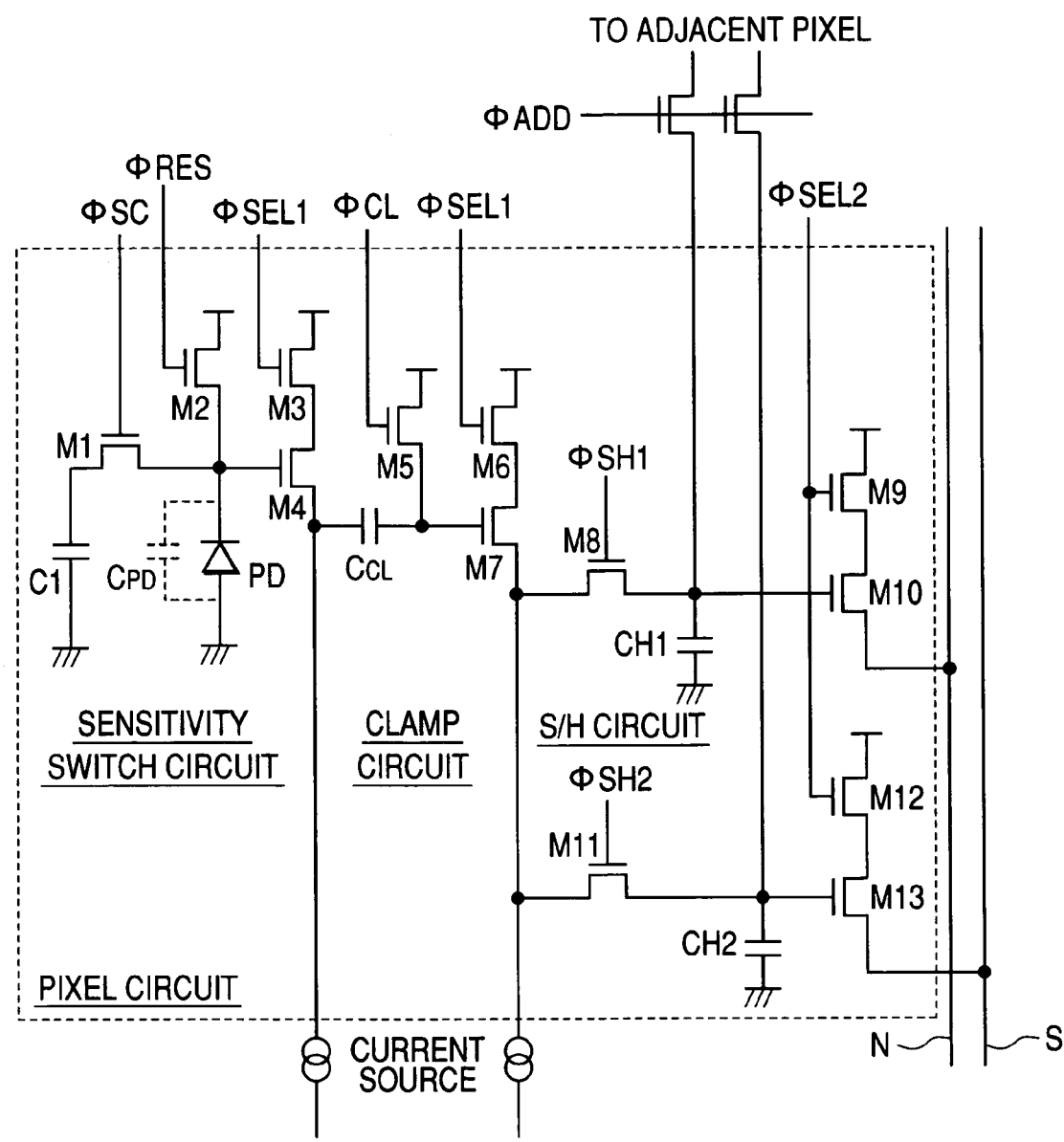
FIG. 19 is a circuit diagram of one pixel of the image pick-up element according to the fifth embodiment of the invention.
Figure 20A:
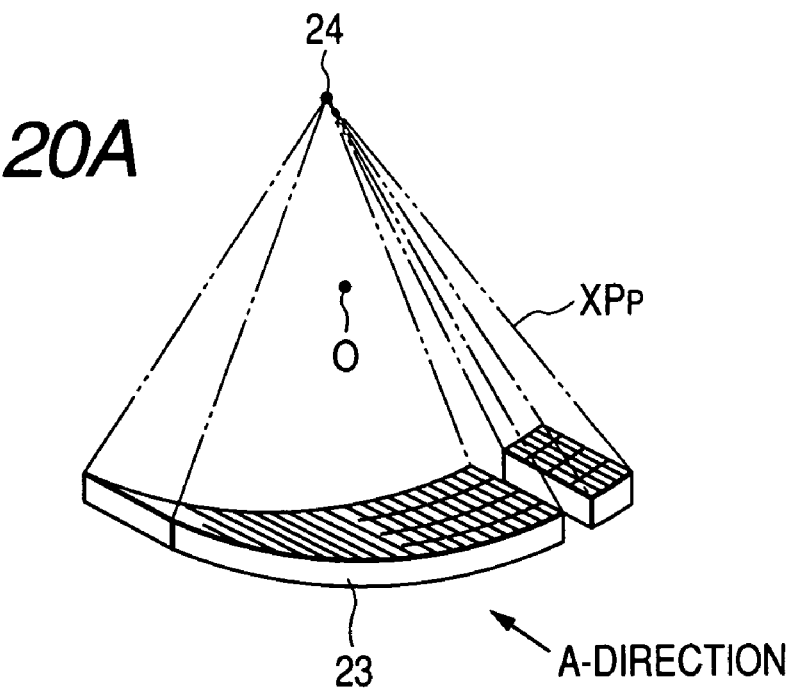
FIGS. 20A and 20B are conceptual diagrams showing a conventional radiation radiographing system.
Figure 20B:
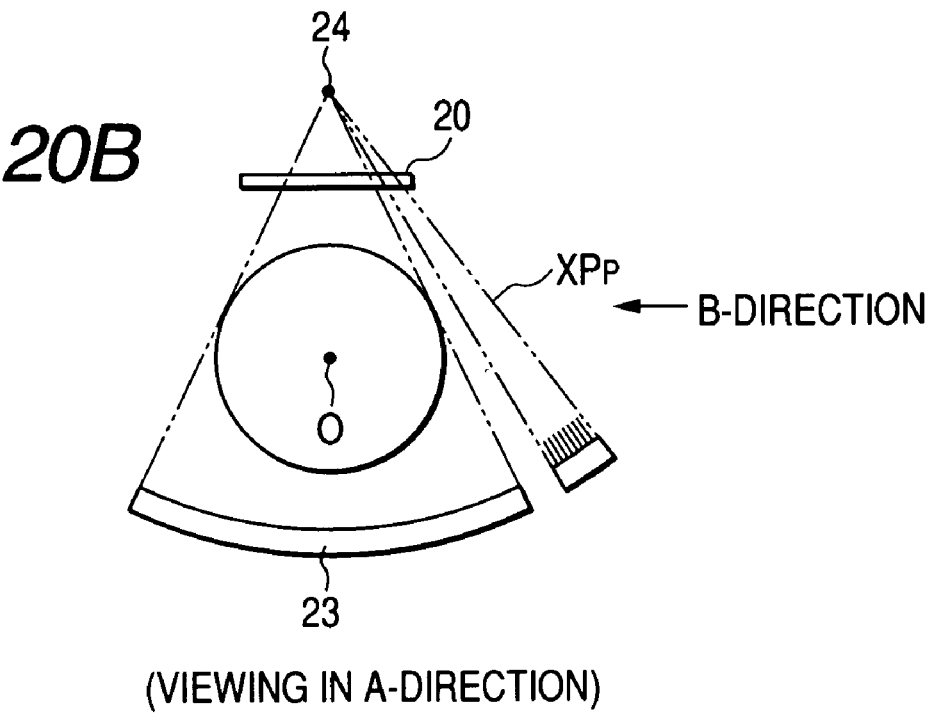

FIG. 18 shows the state where a unit block (unit for selecting and driving one row) of the vertical shift register is arranged in one region (one cell) together with the 1-pixel circuit. The 1-pixel circuit is shown in FIG. 19. An actual element layout is not reflected to the areas of the unit block and the pixel circuit because the diagram shows a schematic diagram. As a vertical shift register, a simple circuit constructed by a static type shift register and a transfer gate in order to form the reset signal φRES, the clamp signal φCL, and the selection signal φSEL1 is shown.

They are driven by the signal from the clock signal line (not shown). The circuit construction of the shift register is not limited to that mentioned above but an arbitrary circuit construction can be used in accordance with various driving methods such as addition reading, decimation reading, and the like. Only three control lines are shown here for simplicity of explanation. The photosignal and the noise signal from each pixel are outputted to a differential amplifier through a column scanning circuit (horizontal shift register, multiplexer) by two signal output lines.

FIG. 19 shows a 1-pixel circuit for realizing the effects of the embodiment. The size of pixel is equal to (160 μm×160 μm) as mentioned above. The capacitor C1 to enlarge the dynamic range is provided for the photodiode PD in parallel therewith. M1 denotes the change-over switch for switching the sensitivity. The photodiode capacitor $C_{PD}$ is designed to the minimum capacitance so as to obtain the maximum sensitivity upon photographing. A capacitance of a gate portion of the amplification MOS transistor M4 to which the photodetector PD is connected is also designed so as to be minimized. M2 denotes the reset MOS transistor (reset switch) to discharge the charges stored in the photodiode PD; M3 the selection MOS transistor (selection switch) to select the pixel amplifier 1; and M4 the amplification MOS transistor (pixel amplifier 1) functioning as a source follower.

The clamp circuit is provided at the post stage of the pixel amplifier 1. The kTC noises which are generated in the photoelectric converting unit are removed by the clamp circuit. The noise removal can be executed by the following operation. That is, by turning on the switch M5, the electrode of the clamp capacitor $C_{CL}$ existing on the amplification MOS transistor M7 (pixel amplifier 2) side is set to a predetermined electric potential.

When the photodiode PD is reset by the reset switch M2 in this state, noise components are stored into the electrode of the clamp capacitor $C_{CL}$ existing on the amplification MOS transistor M4 (pixel amplifier 1) side. By storing the signal charges of the photodiode PD after the turn-on of the switch M5, the electrode potential of the clamp capacitor $C_{CL}$ existing on the pixel amplifier M4 side fluctuates by the amount corresponding to the noise components removed from the signal (containing the noise components) of the photodiode. Also in the amplification MOS transistor M7 (pixel amplifier 2) of the clamp capacitor $C_{CL}$, the electrode potential fluctuates by the amount corresponding to the removed noise components. Thus, the signal from which the noise components are removed is held in the clamp capacitor $C_{CL}$ as mentioned above.

The sampling and holding circuit (S/H circuit) is provided after the clamp circuit. M6 denotes the selection MOS transistor (selection switch) to select the pixel amplifier 2; M8 the sample MOS transistor switch constructing the sampling and holding circuit for storing the photosignal; CH1 the holding capacitor; M10 an amplification MOS transistor (pixel amplifier 3) functioning as a source follower; M9 the selection MOS transistor (selection switch) to select the pixel amplifier 3; M11 the sample MOS transistor switch constructing the sampling and holding circuit for storing the noise signal; CH2 the holding capacitor; M13 the amplification MOS transistor (pixel amplifier 4) functioning as a source follower; and M12 the selection MOS transistor (selection switch) to select the pixel amplifier 4.

The pixels which are arranged so as to be neighboring in the length direction of the vertical output line are connected between the capacitors CH1 and CH2 of the pixel and gates of the pixel amplifiers 3 and 4 through the switches SW10 and SW12 for adding (only the switches and wirings for the image signal are shown in FIG. 17). The pixels which are arranged so as to be neighboring in the direction perpendicular to the length direction of the vertical output line are connected between the capacitors CH1 and CH2 of the pixel and the gates of the pixel amplifiers 3 and 4 through the switch SW11 (only the switches and wirings for the image signal are shown in FIG. 17). This is because since it is a feature of the embodiment that the image signal held in the sampling and holding circuit is added as will be explained hereinafter, it is necessary to provide the switches for adding at this place.

By setting an ADD signal to the high level, all of the switches SW10, SW11, and SW12 are turned on and the connecting points (between the capacitors CH1 and CH2 of the pixel and the gates of the pixel amplifiers 3 and 4) of 16 pixels connected by the switches SW10, SW11, and SW12 are connected in common.

Generally, in the amplifying type image pick-up element such as a CMOS type image pick-up element or the like, the amplifying means (amplifier in the pixel) is provided in the element in order to improve the signal-to-noise ratio (S/N ratio) upon reading, thereby increasing a gain of the signal. In the source follower of the MOS transistor which is generally used as amplifying means, the threshold value Vth of the MOS transistor is liable to vary. Such a variation is peculiar to the design and manufacturing of the element and detrimental because it varies every pixel and every element. Particularly, in the image pick-up element which is used for the X-ray radiographing device is large and the variation in the element is liable to increase. In the case of using a plurality of image pick-up elements, the variation among the elements is large. Such a variation appears as a fixed output fluctuation, that is, what is called a fixed pattern noise (FPN) or an uneven background image.

Since the 1/f noise (flicker noise) or a thermal noise is liable to occur in the MOS transistor and it is a random noise, a random background image occurs. In the device design, assuming that the channel length of the MOS transistor is set to L and the channel width is set to W, since the thermal noise is proportional to $(L/W)\cdot\frac{1}{2}$ and the 1/f noise is inversely proportional to $L\cdot W$, it is preferable to minimize the channel length L and increase the channel width W in order to reduce the noises of the MOS transistor. Particularly, if the channel width W of the source follower serving as an amplifier which becomes a large noise source is set to a large value, the parasitic capacitance between the gate and the drain increases, the gain is decreased, and the sensitivity deteriorates. Therefore, it is difficult to embody the MOS transistor.

In the embodiment, the PMOS transistor whose 1/f noise is essentially small is used at least as a source follower. Consequently, the noise can be reduced to a level of about $\frac{1}{10}$ as compared with that of the NMOS transistor. Even if the X-ray which passed through the scintillator directly collides with the transistor, since the X-ray durability of the PMOS transistor is higher than that of the NMOS transistor (an increase in leakage current and a fluctuation in threshold value Vth are smaller), the PMOS transistor is further preferable.

Since the threshold value Vth changes exponentially in dependence on a temperature, even if each source follower has a temperature difference of 1 degree or less during the photographing, it appears as a fluctuation of the output. In the case of the X-ray radiographing, such a small fluctuation also causes a correction error and becomes a cause of the ring artifact. Therefore, in the two source followers of the sampling and holding circuit, a layout structure in which the variation of the threshold value Vth is as small as possible as a layout is used as will be explained hereinafter, and further, a mechanism in which a temperature difference does not occur during the operation has to be used.

Therefore, there is used a structure in which the sampling and holding (S/H) circuit for the photosignal and the S/H circuit for the noise signal are provided in the pixel as mentioned above, the photosignal and the noise signal are stored independent of the exposure, and the signals are simultaneously outputted (the signals of two lines per column are outputted) from the S/H circuits.

Even if the capacitances of the capacitors CH1 and CH2 are set to be large, the electric potential does not decrease because the front-stage amplifier outputs the voltage. Further, even if the switches SW for adding or the wirings have a floating capacitance, the electric potential does not decrease.

Further, since the capacitances of the capacitors CH1 and CH2 can be increased, even if there is a leakage current in the switches SW for adding or the wirings, the sensitivity is not decreased and the noises do not increase. Since the capacitance CH can be increased as another effect, the MOS transistors (M10, M13) for the source follower for outputting the signals to the vertical output lines can be also increased. Hitherto, if the MOS transistors are increased, the gate capacitance of the MOS transistors causes the decrease in sensitivity, so that it is difficult to enlarge the MOS transistors. Since a shot noise of the MOS transistor is inversely proportional to the ($\frac{1}{2}$)th power of [(channel width W)×(channel length L)], if the channel width W of the MOS transistor is increased, the noises of the source follower for outputting the signals to the vertical output lines can be decreased to a value at which they can be ignored.

Further, as another effect, the shot noise and the 1/f noise of the MOS transistor (pixel amplifier 2) for the source follower which receives the output from the clamp circuit can be also reduced. Since it is desirable to decrease the size of MOS transistor in order to reduce the influence of the gate capacitance of this MOS transistor, the shot noise and the 1/f noise of a certain amount are generated.

In the case of reading out the image by the (1×1) pixel, those noises appear on the output. However, in the case of reading out the projection image by the addition of the (4×4) pixels, since the electric potentials of the individual pixels having those noises can be averaged by the switches SW for adding, the noise voltage decreases. Since the respective random noises are averaged, in the case of the average of 16 pixels, the noises are reduced to the ($\frac{1}{2}$)th power of $\frac{1}{16}$, that is, to $\frac{1}{4}$. In the case where the image is read out by the addition of, for example, (4×4) pixels and the detection signal of the focus movement is read out by the (1×1) pixel of the high resolution as shown in the invention, the image data can be outputted in the state where the noises are reduced in the present image and the priority is given to the resolution in the detection of the focus movement. Therefore, such a layout of the addition switches for connecting the capacitors in the pixel is suitable.

Although the 16 pixels are added in the embodiment, it will be obviously understood that if a construction for adding the larger number of pixels is used, a larger effect will be obtained.

As mentioned above, in the cone beam X-ray CT radiographing using the continuous X-ray, it is necessary to obtain the projection images by driving the whole display surface at the same timing and same storage period. For this purpose, the structure in which the memory is provided in each pixel is used. The projection image signals at the same timing and same storage period are stored into the memories in the pixels and, while the next projection image is obtained, the stored projection data can be read out at a high speed by the parallel reading operation. First, the sampling and holding circuit functions as means (memory in the pixel) for storing the image signal independent of the exposure as mentioned above. The cone beam X-ray CT radiographing of the large area which could not be realized hitherto can be realized by the foregoing parallel reading operation of the image pick-up elements and those structures and functions.

Further, the circuit has the noise removing function. Since the photosignal and the noise signal are fetched into the S/H circuit from the pixel amplifier 1 at the very small time difference, the large 1/f noise of the low frequency can be ignored.

The thermal noise, 1/f noise, and FPN in the pixel amplifier are removed by using the circuit. The variation of the two S/H circuit elements is reduced as much as possible by the method whereby the capacitors are arranged at the closest positions in the pixel, the source followers of the outputs are arranged in the cross layout which is used in the ordinary MOS circuit layout, and the variation of the threshold value Vth is reduced as much as possible. As mentioned above, the S/H circuit functions as storing means of every pixel for the batch-exposure, and also functions as noise removing means.

In the embodiment, the control of the timing for obtaining each projection image is made by using the angle signal which is outputted from the rotary encoder 103. The reading switch and the reset switch are driven by the pulse signals formed by the storage period controller 208 on the basis of the angle signal from the rotary encoder 103. The angle signal which is outputted from the rotary encoder 103 is sent to the storage period controller 208. The timing pulse for the batch-reset and the operation timing pulse for the batch-exposure are formed on the basis of this signal. Those operation timing and the operation timing of the S/H circuit are controlled and the projection image signal is stored and outputted for the storage period corresponding to the angle of one projection so that a time lag is not caused in each projection image. Thus, even if there is a rotational variation in the rotating plate, the projection image of the period corresponding to the rotational angle per projection which has accurately been determined can be obtained.

The X-ray CT image is obtained in correspondence to the storage period according to the rotational angle of one projection of the rotating plate 102. At this time, the ADD signal is always held at the low level and the switches SW10, SW11, and SW12 are set to OFF. The storing operation is independently executed with respect to all of the pixels. It is one of the features of the embodiment. The images of one projection are obtained with respect to all of the pixels and held in the S/H circuit.

The image signal corresponding to the edge detecting region in the image is read out at the resolution of (1×1) pixel prior to executing the reading operation. As shown in FIG. 16, when the focal point of the X-ray source is moved, the image of the edge of the edge block 901 also moves on the X-ray image sensor panel 101. Since it is unpreferable to newly attach the edge block 901 to the X-ray source side for the general photographing, it is provided as an optional block for the rotating device. In this case, L1<L2. In the case of the CT radiographing, since the operator wants to reduce the cone angle, there is such a tendency that L2 is fairly longer than L1. Assuming that L2=2 m and L1=1 m, since the focus movement of the X-ray source generally occurs in a range of about 500 μm to 1 mm, the movement on the X-ray image sensor panel lies within a range of about 250 μm to 500 μm.

In the case of the ordinary pixel size which is used in the X-ray CT radiographing, the focus movement cannot be accurately detected. Therefore, in the invention, a change in edge position corresponding to the focus movement of the X-ray source is obtained at high resolution of a pitch of 160 μm. Naturally, by setting the pixel size to a value smaller than 160 μm, the edge can be more accurately detected.

It is an essence of the embodiment that by setting the pixel size of the resolution higher than that of the pixel size of the X-ray CT radiographing image, the focus movement of the X-ray can be accurately detected at the higher resolution. In this instance, however, the embodiment is characterized in that the non-destructive reading operation is executed so as not to exert any influence on the main image. The image in this instance differs from the main image with respect to only the resolution and the image data stored for the same storage period from the same timing is used. Therefore, the data in the S/H circuit in the pixel is used. The means for non-destructively reading out the image data is the source follower circuit including the transistors M10 and M13 in FIG. 19. The embodiment is characterized in that the S/H circuit is provided in the pixel and the source follower circuit serving as non-destructive reading means is provided after the S/H circuit.

Since all of the pixels in the limited region are merely read out, they can be read out at a high speed at which it does not exert an influence on the whole image reading. Since the image signals before the pixel addition are non-destructively read out, the stored image signal is not influenced at all. After the edge detecting portion is read out as mentioned above, by reading out the ADD signal, that is, by setting the ADD signal to the high level at the time of outputting the projection image, all of the switches SW10, SW11, and SW12 are turned on. The connecting points (between the capacitors CH1 and CH2 and the gates of the pixel amplifiers 3 and 4) of 16 pixels connected by the switches SW10, SW11, and SW12 are connected in common, the signals of (4×4) pixels are added, and the addition signal is outputted.

Since the resolution at this time is equal to (640 μm×640 μm), it is preferable to the X-ray CT image. The image of a large area exceeding (40 cm×40 cm) can be obtained at a high speed exceeding 200 frames/sec owing to the parallel reading of the image pick-up elements, the batch-exposure using the S/H circuit, and the addition of (4×4) pixels.

According to the embodiment, although the resolution at the time of the storing operation is set to be higher than that upon reading, it is preferable to use the highest resolution for the edge detection. In other words, it is desirable to read out on a unit basis of the minimum pixel of the image pick-up element.

The specific operation of the embodiment will now be described. The photoelectric conversion is executed by the photodiode PD. As for the exposure, the batch-exposure is performed at the same timing and same period with respect to all of the pixels of each image pick-up element. Therefore, no time-dependent deviation of the images occurs among the image pick-up elements and among the scanning lines. The signal corresponding to the start angle of the N-th projection is sent from the rotary encoder 103 to the storage period controller. By simultaneously setting the signal φSH1 to the high level and turning on the sample switch M8 in a lump by the storage period controller with respect to all of the pixels, the photosignal which has been stored in the previous projection and from which the noises have been removed is transferred in a lump into the capacitor CH1 through the pixel amplifier 2 (M7).

By setting the signal φRES to the high level and turning on the reset switch M2 in a lump with respect to all of the pixels, the photodiode capacitor $C_{PD}$ is reset. The signal storage corresponding to the N-th projection starts from the end point of the resetting operation. Since the signal φSH1 is controlled by the storage period controller and the other signals are determined in response to φSH1, the signal storage in the photodiode is controlled every projection.

At the same time, by setting the signal φCL to the high level and turning on the clamp switch M5, the clamp capacitor $C_{CL}$ is set to the reference voltage. At the same time, by setting the signal φSH2 to the high level and turning on the sample switch M11 in a lump with respect to all of the pixels, the noise signal when the circuit is set to the reference voltage is transferred to the capacitor CH2.

Subsequently, by setting the signal φSH2 to the low level, the transfer and holding of the photosignal and the noise signal into the S/H circuit are finished. At this stage, the image signal of the N-th projection has been stored in the sampling and holding capacitor in the state of (1×1) pixel.

Subsequently, the selection signal φSEL2 corresponding to the edge detecting region is set to the high level. By turning on the selection switches M9 and M12 of the corresponding pixel, the source follower circuit constructed by the load current source and the pixel amplifiers 3 and 4 (M10 and M13) is made operative. Thus, the photosignal and the noise signal held in the holding capacitors CH1 and CH2 are simultaneously outputted to the photosignal output line and the noise signal output line through the pixel amplifiers 3 and 4.

While each of the selection signals is at the high level, the vertical output line corresponding to the edge detecting region is selected by the horizontal scanning circuit (Mux) and the signal outputted to each vertical output line is outputted as an output signal (out). Since the non-destructive reading is executed in this instance, the signals held in the holding capacitors CH1 and CH2 at the timings before and after the reading operation are not influenced. Further, since the limited region is read out at a high speed, the main reading operation of the image signal is not influenced.

Subsequently, the ADD signal is set to the high level and the switches SW10, SW11, and SW12 are turned on. Thus, the electric potential of the capacitor CH of each pixel becomes the average potential of the electric potentials of the capacitors CH in the respective pixels before the addition of the unit of (4×4) pixels, that is, 16 pixels.

Subsequently, the selection signal φSEL2 which is outputted from the shift register (SR) is sequentially set to the high level every four rows. The signals held in the capacitors CH are amplified and outputted to the vertical output lines from the group of pixels which have been arranged in the horizontal direction and to which the selection signals are supplied. At this time, since the electric potentials of the capacitors CH 1 and CH2 are the same on a 16-pixel unit basis, there is no need to set the selection signals φSEL2 of all rows to the high level.

The signals outputted to the vertical output lines are selected every other three lines by the horizontal scanning circuit (Mux) while each selection signal is at the high level. An average value of 16 pixels is outputted as an output signal (out).

In the case of mainly reading the image data, since it is read out in the addition mode and only the output corresponding to 1/16 of all pixels is outputted, a reading speed can be multiplied by about 16 times.

In the embodiment, In place of the shift register, the n-to-$2^n$ decoder can be also used as a scanning circuit. In this case, by connecting the output of the counter which is sequentially incremented to the input of the decoder, it is possible to sequentially scan in a manner similar to the shift register. By inputting the address of the region where the operator wants to obtain the image into the input of the decoder, the image of the arbitrary region by the random scan can be obtained. The common processing circuit which is arranged in each region (cell) in the valid region denotes the circuit for batch-processing in common a plurality of component elements such as final-signal output amplifier, serial/parallel conversion multiplexer, buffer, various gate circuits, and the like.

In the embodiment, by arranging the photosensing regions of the uniform size in each image pick-up element and among the image pick-up elements so that the centers of gravity are arranged at an equal pitch, even if the shift registers and the like are arranged in the valid region, the sensitivity variation and the variation of the centers of gravity of the photosensing regions do not occur among the image pick-up elements and in the image pick-up element. Thus, even in the construction in which a plurality of image pick-up elements are adhered like a tile, the image which is substantially seamless can be obtained. Since no dead spaces are caused around the image pick-up element, the whole surface of the image pick-up element becomes the valid region.

By arranging the image pick-up elements like a tile without substantially causing any gap, the image pick-up device of a large area can be formed. Further, by using such a circuit construction as mentioned above, the image of a large area which is substantially seamless with respect to the time and space can be obtained. Since the size of pixel is sufficiently large, even if the shift register is arranged in the valid pixel region or even if the circuit such as a sampling and holding circuit is arranged in the pixel, a sufficiently large numerical aperture can be realized. Therefore, no problem occurs.

Since the shift registers are arranged in the valid region in the embodiment, the X-ray which passed through the scintillator directly collides with the shift register. However, by using the static shift register as a shift register, an influence by the X-ray is not exercised. The shift register circuit is used to sequentially transfer the pulse signals. That is, since the static type shift register is relatively difficult to be influenced by the X-ray in principle, it can be used at the place where the X-ray directly collides with it. Therefore, by using the static type shift register, the image pick-up device in which an X-ray damage and an error are small and the reliability is improved can be realized.

Further, since the CMOS type image pick-up element is used as an image pick-up element in the embodiment, electric power consumption is small and it is suitable to the case of constructing the image pick-up device of a large area. The reason why the multiplexer is formed in the image pick-up element is to raise the operating speed in the image pick-up element. The signal is extracted from the image pick-up element to the outside through the electrode pad. However, there is a large floating capacitance around the electrode pad. Therefore, by providing the amplifier for the front stage of the electrode pad, the transmitting characteristics of the signal can be compensated.

In the embodiment, the kTC noises are generated upon resetting of the photoelectric converting unit because the signals are not perfectly transferred. As a circuit, removal of the kTC noises is an important point to realize the high S/N ratio of the photoelectric converting device. In the embodiment, therefore, the clamp circuit is provided every pixel. Use of the clamp circuit to remove the kTC noises is well known. In the case where the pixel size is relatively small and the perfect transfer is possible, since no kTC noises are generated in the photoelectric converting unit, it is not always necessary to provide such a clamp circuit.

In the embodiment, the clamp circuit is provided at the front stage of the S/H circuit for the batch-exposure so that the kTC noises can be removed by the batch-exposure. Further, since the fixed pattern noise (FPN) upon resetting of the photoelectric converting unit can be removed, the sensitivity can be further improved.

It is desirable that the capacitance $C_{PD}$ is large in order to increase the dynamic range. However, if it is large, since the signal voltage drops, the S/N ratio deteriorates. To widen the dynamic range upon photographing of the still image while maintaining the highest sensitivity upon photographing, a sensitivity (dynamic range) switch circuit is provided and the capacitor and the change-over switch are provided for each pixel. Since the capacitance increases upon the photographing of the still image, the S/N ratio deteriorates. However, the clamp circuit for removing, particularly, the kTC noises is necessary to improve the S/N ratio.

A collecting procedure of the projection images of one rotation of the object in the object rotating type cone beam X-ray CT radiographing device according to the embodiment will now be described. First, the observer fixes the object 107 to the holding device. Subsequently, when the observer instructs to start the measurement from the operation panel (not shown), the measurement of the projection image (projection data) is started by the control signal outputted from the radiographic control device 105 and the rotating plate 102 starts the rotation. At this time, the rotational angle is outputted from the rotary encoder 103 to the radiographic control device 105.

When it is detected that the rotational angle of the rotating device 102 has reached the predetermined angle, the radiographic control device 105 allows the X-ray generator 109 to immediately radiate the continuous X-ray. In association with the radiation of the X-ray from the X-ray generator 109, the radiographic control device 105 obtains the production image of the object 107 by controlling the X-ray image sensor panel 101.

The production image is outputted as digital production data to the radiographic control device 105. The radiographic control device 105 collects the production image photographed by the X-ray image sensor panel 101 together with the rotational angle of the rotating device 102, that is, projection angle, stores them into the image data memory 203, and subsequently executes such an operation every predetermined angle, thereby finishing the photographing of the production images of one rotation.

After the photographing (collection) of the production images of the whole circumference is finished, the radiographic control device 105 finishes the rotation of the rotating device 102. In the image processing unit 202, the following preliminary processes are executed to the production images stored in the image data memory by using the correction data which has already been stored in the correction data memory. That is, the gamma correction, image distortion correction, logarithm conversion, sensitivity variation correction of the X-ray image sensor panel, and the like are executed to each production image. Further, a 3-dimensional X-ray distribution image is reconstructed on the basis of the production images. Moreover, the image process such as well-known volume rendering process, maximum value projecting process, or the like is executed to the 3-dimensional X-ray distribution image. A 3-dimensional X-ray image as a 3-dimensional-like 2-dimensional is formed from the 3-dimensional X-ray distribution image. The 3-dimensional X-ray image is displayed onto the display screen of the display 106.

The operation and effects will now be described. A special focus movement detector is unnecessary. The X-ray image sensor panel can be used as it is. There is no need to prepare the detector on the X-ray source side. It is convenient in the case of using the X-ray source for the general photographing as an X-ray source.

Since the mode of the X-ray image sensor panel can be non-destructively switched (resolution can be switched), in the case of detecting the focus movement, since the resolution can be freely changed as compared with that upon obtaining of the image upon setting of the high resolution, the focus movement can be more accurately detected. In the case of the embodiment, the data after the storage by the batch-exposure is used. Therefore, the non-destructive reading means is necessary after the pixel memory (sampling and holding circuit). Since the data held in the S/H circuit is not destroyed, the data obtained by the main reading operation and the data obtained by the non-destructive reading have the same value except for the resolution. The noises and the like are not added. The image data having the common storage period can be non-destructively read out by changing the resolution (without changing the noises and the like). In the case of the ordinary non-destructive reading, the method of reading the fluctuating signal of the photodiode PD or the like (to monitor the exposure amount or the like) is used. However, a method different from such a method is used in the embodiment.

Since the location to detect the focus movement is limited, by locally non-destructively reading out the image data, it can be read out at a high speed. The actual measuring speed is not sacrificed. Since the random access and the non-destructive reading can be performed, an arbitrary blank portion of the X-ray image sensor panel can be selected. If the ROI has preliminarily been known, a diaphragm is provided to reduce the radiation exposure. At this time, an arbitrary blank portion in the ROI can be also selected. As for the edge showing the focus movement, in the case of properly adjusting the position, the detecting location of the panel can be arbitrarily changed in accordance with the adjusted position.

Sixth Embodiment

Figure 15:
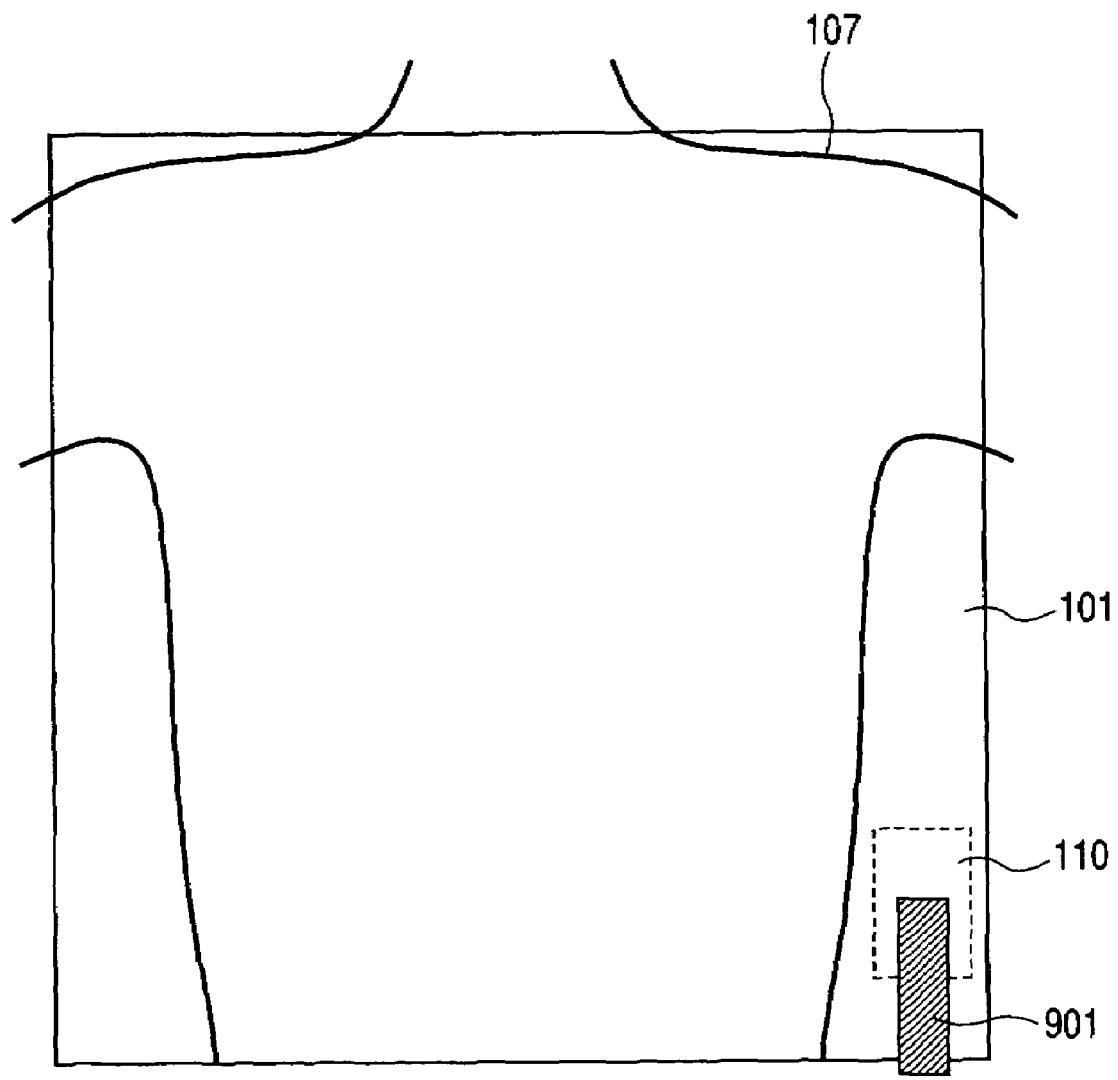
FIG. 15 is a diagram for explaining a projection image.

According to the sixth embodiment, a collimator is arranged in the edge detecting region on the X-ray image sensor panel 101. The operation of the X-ray image sensor panel 101 is substantially the same as that in the first embodiment. As shown in FIG. 15, the projection image includes the portions without a projection image of the object, that is, the blank portions. The region surrounded by the broken line among the blank portions is used as a reference signal detecting portion 110. This region is determined by radiating the very weak X-ray prior to the main scanning and detecting the blank portions. After the reference signal detecting portion is determined, a collimator for removing the scattered lines from the object is set to the relevant location of the X-ray image sensor panel. A grid can be also used in common. Other constructions are similar to those in the fifth embodiment.

In the sixth embodiment, since the collimator is used to eliminate the scattering lines, the blur of the edge can be suppressed. The focus movement can be detected at high precision owing to the high resolution and the non-destructive reading. The collimator and the edge can be also used in common. Further, since L2 decreases, the higher resolution is demanded. However, according to the X-ray image sensor panel of the invention, such a small edge movement can be also detected.

Seventh Embodiment

According to the seventh embodiment, in the object rotating type cone beam X-ray CT radiographing system, in the case of setting the rotating plate 102 and the X-ray image sensor panel 101 to the existing X-ray generator 109 for the general photographing, their geometrical layout is precisely determined. The X-ray generator 109, rotating plate 102, and X-ray image sensor panel 101 are movable and after their geometrical layout is determined, their positions are fixed. In the cone beam X-ray CT radiographing device, when the cone angle increases, the errors upon reconstruction increase. Therefore, the cone angle Φ is generally set to 10° or less.

There are various possibilities in such a layout in accordance with a size of general photographing room or the like. When the distance between the X-ray focal point and the rotary axis P of the rotating plate 102 is set to L and the distance between the rotary axis and the X-ray image sensor panel 101 is set to M, there is also a case where the values of L and M vary every layout. In such a case, the enlargement ratio of the projection image changes. In the conventional detector for the X-ray CT, the resolution is fixed and the enlargement ratio cannot cope with the change. In the embodiment, the X-ray image sensor panel whose resolution can be arbitrarily changed is used. This fundamental construction is similar to that of the X-ray image sensor panel used in the fifth embodiment. By changing the pixel adding mode, the change in resolution can be arbitrarily set. The system has five fundamental modes of (1×1), (2×2), (3×3), (4×4), and (5×5). Other constructions are similar to those in the fifth embodiment.

In the seventh embodiment, naturally, the operations and effects as mentioned in the fifth embodiment are obtained and the picture quality is not influenced by the selection of the adding mode. The high sensitivity and high operating speed which are suitable for the cone beam X-ray CT radiographing are also obtained. After the geometrical layout of the X-ray generator 109, rotating plate 102, and X-ray image sensor panel 101 is precisely determined, the adding mode is changed in accordance with the enlargement ratio. The fundamental mode of (4×4) is set as a default. Actually, the values of L and M are set so as to meet one of the five adding modes. That is, a marker is attached onto the rotating plate and, while its enlargement ratio is measured by the X-ray image sensor panel, an optimum one of the combinations of the adding modes of L and M is selected.

In the case of using the grid, a relation with the focal point of the grid is also considered. The optimum grid can be also selected after the values of L and M are determined. The resolution can be also changed with respect to the rotational plane direction and the boxy axial direction. Further, it is also possible to start the photographing at the default resolution set by the above method and change it during the photographing. For example, since necessary information amounts in a coronal image and a sagittal image after the reconstruction differ, it is possible to optimize the resolution at the time of the rotation and obtain the projection image, or the reconstruction time can be shortened by reducing the resolution during the measurement of the side surface of the object and decreasing the information amount. The influence on the image of the side surface after the reconstruction due to the decrease in information is smaller than those on the front and rear images. In the case of the medical examination, it is an important subject to shorten the reconstruction time.

According to the embodiments, the default X-ray CT image can be obtained irrespective of the geometrical layout and the cone beam X-ray CT radiographing device suitable for the movable system can be provided.

This application claims priority from Japanese Patent Application Nos. 2004-086884 filed Mar. 24, 2004 and 2004-092223 filed on Mar. 26, 2004, which are hereby incorporated by reference herein.

What is claimed is:

1. A radiation CT radiographing device comprising:
   rotating means for rotating an object to be irradiated with a radiation;
   rotational angle detecting means for detecting a rotational angle of said rotating means and generating a rotational angle signal;
   a radiation image sensor panel for forming projection image data of the object based on the rotation; and
   controlling means for controlling a storage period of said radiation image sensor panel based on the rotational angle signal, wherein,
   when a change in a time period for a rotational angle of said rotating means occurs during one projection of the radiation, said controlling means changes the storage period for the one projection of said radiation image sensor panel to adapt the storage period to the change in the time period for the rotational angle of said rotating means during one projection of the radiation.

2. A radiation CT radiographing device according to claim 1, further comprising
   a reference signal generation means which comprises a conversion element for converting the radiation into an electric signal, and a circuit for storing the electric signal from the conversion element and outputting an integrated quantity of the electric signal.

3. A radiation CT radiographing device according to claim 2, wherein
   the radiation is a continuous radiation emitted from a radiation source, the reference signal generation means is disposed between the radiation image sensor panel and the radiation source, and wherein,
   when the change in a time period for a rotational angle of said rotating means occurs during one projection of the radiation, said controlling means changes the storage period for the one projection of said radiation image sensor panel to adapt the storage period to the change in the time period for the rotational angle of said rotating means during one projection of the radiation, and changes the storage period of said reference signal generation means.

4. A radiation CT radiographing device according to claim 2, wherein
   the radiation is a continuous radiation emitted from a radiation source, said radiation image sensor panel comprises a plurality of image pick-up elements, each image pick-up element comprising a plurality of pixels, and said reference signal generation means is one or some of the plurality of pixels, and wherein,
   when the change in a time period for a rotational angle of said rotating means occurs during one projection of the radiation, said controlling means changes the storage period for the one projection of said radiation image sensor panel to adapt the storage period to the change in the time period for the rotational angle of said rotating means during one projection of the radiation, and changes the storage period of said reference signal generation means.

5. A radiation CT radiographing device according to claim 1, wherein
   said rotational angle detecting means generates the rotational angle signal responsive to a detection of a predetermined rotational angle of said rotating means during one projection of the radiation.

6. A radiation CT radiographing device according to claim 1, further comprising:
   calculation means for calculating storage period data corresponding to the storage period;
   white image data storage means for storing a white image data derived from said radiation image sensor panel by irradiating said radiation image sensor panel with the radiation not through the object;
   FPN image data storage means for storing a FPN image data derived from said radiation image sensor panel without irradiating said radiation image sensor panel; and
   correction means for a white correction and a FPN correction of each of projection image data based on the storage period data, the white image data, and the FPN image data.

7. A radiation CT radiographing device according to claim 6, wherein
   said correction means performs the correction of each of projection image data further based on a signal data of a reference signal generation means, wherein the reference signal generation means comprises a conversion element for converting the radiation into an electric signal, and a circuit for storing the electric signal from the conversion element and outputting an integrated quantity of the electric signal.

8. A radiation CT radiographing device comprising:

rotating means for rotating an object to be irradiated with a radiation;

rotational angle detecting means for detecting a rotational angle of said rotating means and generating a rotational angle signal;

a radiation image sensor panel fixed relatively to an axis of the rotation while forming projection image data of the object based on said rotation; and controlling means for controlling a storage period of said radiation image sensor panel based on said rotational angle signal, wherein, when a change in a time period for a rotational angle of said rotating means occurs during one projection of the radiation, said controlling means changes the storage period for the one projection of said radiation image sensor panel to adapt the storage period to the change in the time period for the rotational angle of said rotating means during one projection of the radiation.

9. A radiation CT radiographing device according to claim 8, further comprising a reference signal generation means which comprises a conversion element for converting the radiation into an electric signal, and a circuit for storing the electric signal from the conversion element and outputting an integrated quantity of the electric signal, wherein the radiation is a continuous radiation emitted from a radiation source, said reference signal generation means is disposed between said radiation image sensor panel and the source, and wherein, when the change in a time period for a rotational angle of said rotating means occurs during one projection of the radiation, said controlling means changes the storage period for the one projection of the radiation image sensor panel to adapt the storage period to the change in the time period for the rotational angle of said rotating means during one projection of the radiation, and changes the storage period of said reference signal generation means.

10. A radiation CT radiographing device according to claim 8, further comprising:

calculation means for calculating storage period data corresponding to the storage period;

white image data storage means for storing a white image data derived from said radiation image sensor panel by irradiating said radiation image sensor panel with the radiation not through the object;

FPN image data storage means for storing a FPN image data derived from the radiation image sensor panel without irradiating said radiation image sensor panel; and correction means for a white correction and a FPN correction of each of projection image data based on the storage period data, the white image data, and the FPN image data.

11. A radiation CT radiographing system comprising:

a radiation source for irradiating an object with a radiation;

radiation source control means for controlling the radiation source;

rotating means for rotating the object to be irradiated with a radiation;

rotational angle detecting means for detecting a rotational angle of said rotating means and generating a rotational angle signal;

a radiation image sensor panel comprising a plurality of pixels and forming projection image data of the object based on the rotation; and controlling means for controlling a storage period of the pixels based on the rotational angle signal, wherein, when a change in a time period for a rotational angle of said rotating means occurs during one projection of the radiation, said controlling means changes the storage period for the one projection of the pixels to adapt the storage period to the change in the time period for the rotational angle of said rotating means during one projection of the radiation.

12. A radiation CT radiographing method comprising steps of:

rotating an object while irradiating the object with a radiation, detecting a rotational angle of the object and generating a rotational angle signal, wherein, when a change in a time period for a rotational angle of said rotating means occurs during one projection of the radiation, a storage period of a radiation image sensor for the one projection is changed to adapt the storage period to the change in the time period for the rotational angle during one projection of the radiation.

13. A radiation CT radiographing method according to claim 12, wherein when the change in a time period for a rotational angle in said rotating step occurs during one projection of the radiation, the storage period of the radiation image sensor panel for the one projection and a storage period of a reference signal generation means are changed to adapt them to the change in the time period for the rotational angle during one projection of the radiation, wherein the reference signal generation means comprises a conversion element for converting the radiation into an electric signal, and a circuit for storing the electric signal from the conversion element and outputting an integrated quantity of the electric signal.

14. A radiation CT radiographing method according to claim 13, further comprising a step of correcting the projection image data based on a storage period data calculated correspondingly to the storage period, a white image data derived by irradiating the radiation image sensor panel with the radiation not through the object, and a FPN image data derived without irradiating the radiation image sensor panel.

* * * * *

UNITED STATES PATENT AND TRADEMARK OFFICE
CERTIFICATE OF CORRECTION

PATENT NO.       : 7,310,404 B2                                            Page 1 of 1
APPLICATION NO.  : 11/084130
DATED            : December 18, 2007
INVENTOR(S)      : Kazuaki Tashiro et al.

It is certified that error appears in the above-identified patent and that said Letters Patent is hereby corrected as shown below:

COLUMN 3

Line 62, "an" should read --a--.

COLUMN 23

Line 29, "1001." should read --101.--.

COLUMN 31

Line 34, "In place" should read --in place--.

COLUMN 36

Line 4, "comprising" should read --comprising:--.

COLUMN 37

Line 27, "comprising" should read --comprising:--.

Signed and Sealed this

Eleventh Day of November, 2008

JON W. DUDAS
*Director of the United States Patent and Trademark Office*